US008222441B2

(12) United States Patent
Lin et al.

(10) Patent No.: US 8,222,441 B2
(45) Date of Patent: Jul. 17, 2012

(54) PHOSPHORUS-CONTAINING COMPOUNDS AND THEIR PREPARING PROCESS AND USE

(75) Inventors: Ching-Hsuan Lin, Taichung (TW); Tsung Li Lin, Hsinchu County (TW); Chia Wei Chang, Hsinchu County (TW); Kuen-Yuan Hwang, Hsinchu County (TW); An-Pang Tu, Hsinchu County (TW); Fang-Hsien Su, Hsinchu County (TW)

(73) Assignees: Chang Chun Plastics Co., Ltd., Hukou Township, Hsinchu County (TW); National Chung Hsing University, Taichung (TW)

( * ) Notice: Subject to any disclaimer, the term of this patent is extended or adjusted under 35 U.S.C. 154(b) by 438 days.

(21) Appl. No.: 12/385,573

(22) Filed: Apr. 13, 2009

(65) Prior Publication Data

US 2009/0258997 A1    Oct. 15, 2009

(30) Foreign Application Priority Data

Apr. 11, 2008    (TW) .............................. 97113431 A

(51) Int. Cl.
C07F 9/32 (2006.01)
C08L 71/02 (2006.01)
(52) U.S. Cl. .......................................... 558/82; 525/409
(58) Field of Classification Search .................... 558/82; 525/409
See application file for complete search history.

(56) References Cited

U.S. PATENT DOCUMENTS

| 2003/0120021 A1 | 6/2003 | Wang et al. |
| 2006/0194045 A1 | 8/2006 | Masuda |
| 2008/0045688 A1 | 2/2008 | Lin et al. |

FOREIGN PATENT DOCUMENTS

| EP | 1 612 244 A1 | 3/2004 |
| EP | 1 889 878 A1 | 5/2006 |
| TW | 200637901 | 11/2006 |

OTHER PUBLICATIONS

Lin et al. "Facile preparation of novel epoxy curing agents and their high-performance thermosets" Journal of Polymer Science, Part A: Polymer Chemistry, 2008, vol. 46, No. 23, pp. 7898-7912.*
Cai et al. "Flame-retardant epoxy resins with high glass-transition temperatures from a novel trifunctional curing agent: Dopotriol" Journal of Polymer Science, Part A: Polymer Chemistry, 2005, vol. 43, No. 13, pp. 2862-2873.*
Ching Hsuan Lin et al., "Flame-Retardant Epoxy Resins with High Glass-Transition Temperatures. II. Using a Novel Hexafunctional Curing Agent: 9, 10-Dihydro-9-oxa-10-phosphaphenanthrene 10-yl-tris(4-aminophenyl) methane", Journal of Polymer Science: Part A: Polymer Chemistry, vol. 43, 2005, pp. 5971-5986.
Sheng Xiong Cai et al., "Flame-Retardant Epoxy Resins with High Glass-Transition Temperatures from a Novel Trifunctional Curing Agent: Dopotriol", Journal of polymer Science: Part A: Polymer Chemistry, vol. 43, 2005, pp. 2862-2873.
European Search Report mailed Oct. 20, 2009.
Sheng Xiong Cai et al., "Flame-Retardant Epoxy Resins with High Glass-Transition Temperatures From a Novel Trifunctional Curing Agent: Dopotriol", Journal of Polymer Science: Part A: Polymer Chemistry, vol. 43 (2005), pp. 2862-2873.
Ching Hsuan Lin et al., "Flame-Retardant Epoxy Resins with High Glass-Transition Temperatures. II. Using a Novel Hexafunctional Curing Agent: 9,10-Dihydro-9-oxa-10-phosphaphenanthrene 10-yl-tris (4-aminophenyl) Methane", Journal of Polymer Science: Part A: Polymer Chemistry, vol. 43 (2005), pp. 5971-5986.
Ching Hsuan Lin et al., "Synthesis and Properties of Flame-Retardant Benzoazines by Three Approaches", Journal of Polymer Science: Part A: Polymer Chemistry, vol. 44 (2006), pp. 3454-3468.
Ching Hsuan Lin et al., "Flame-Retardant Epoxy Resins with High Glass-Transition Temperatures. II. Using a Novel Hexafunctional Curing Agent: 9,10-Dihydro-9-oxa-10-phosphaphenanthrene 10-yl-tris (4-aminophenyl) methane", *Journal of Polymer Science*, Part A: Polymer Chemistry, vol. 43 (23) /2005; pp. 5971-5986.

* cited by examiner

*Primary Examiner* — Joseph Kosack
(74) *Attorney, Agent, or Firm* — Stites & Harbison, PLLC; Juan Carlos A. Marquez, Esq

(57) ABSTRACT

A series of novel phosphorus-containing compounds having the following formula are disclosed:

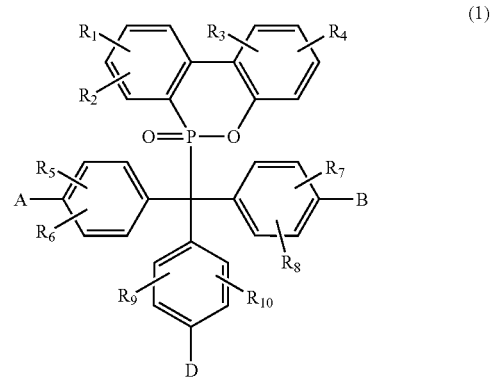

wherein
$R_1$-$R_{12}$, A, B, D, X, and Y are as defined in the specification.
A process for the preparation of the compound of formula (1), a curing agent, and a flame resistant epoxy resin and a preparation process thereof are also provided.

19 Claims, 10 Drawing Sheets

PHOSPHORUS-CONTAINING COMPOUNDS AND THEIR PREPARING PROCESS AND USE

FIELD OF THE INVENTION

The present invention discloses phosphorus-containing compounds which can be used as curing agents for epoxy resins and in the preparation of a flame resistant cured epoxy resin.

DESCRIPTION OF THE PRIOR ART

Epoxy resins have advantages such as excellent electrical properties, shape stability, resistance to high temperature and solvent, low cost and high adherence, and are most suitable for use as packaging materials for printed circuit boards and integrated circuits. However, like general plastic materials, epoxy resins combust easily and thus pose a threat to human life. Thus, there is a strict requirement for the flame retardancy of the electronic materials all over the world. Bromine-containing epoxy resins are especially suitable for the circuit boards with flame resistance. These bromine-containing epoxy resins, however, will release corrosive and toxic substances such as tetrabromodibenzo-p-dioxin and tetrabromodibenzofuran during combustion. In addition to halogen-containing compounds, another approach is to coat an additional non-flammable layer outside the plastics.

Among these flame resistant compounds, organophosphorus compounds have high flame retardancy. Phosphorus-containing flame resistant agents will facilitate dehydration of polymer materials in advance in combustion, allowing the hydrogen of the hydrocarbons to react with oxygen in the air to form water, thereby reducing the ambient temperature to below the combustion temperature and achieving a flame resistant effect; on the other hand, the phosphorus-containing flame resistant agents are decomposed to form phosphoric acid on heating at elevated temperature, which facilitates the carbonization of polymers to form a non-flammable coke layer. Furthermore, phosphoric acid will be dehydrated and esterified at elevated temperature to form polyphosphoric acid, which covers the surfaces of the combustion substances, prevents oxygen gas from entering the uncombusted inner layer of the polymers, and inhibits the release of volatile cracked products.

There are two ways to introduce phosphorus elements into polymers. One is to synthesize phosphorus-containing epoxy resins, and the other is to synthesize phosphorus-containing curing agents. The present invention utilizes a manner of synthesizing novel phosphorus-containing curing agents, so that epoxy resins are cured to achieve the flame resistant effect.

Among phosphorus-containing reactants, the reactive 9,10-dihydro-9-oxa-10-phosphaphenanthrene 10-oxide (DOPO) is of particular interest since it can react with electron-deficient compounds such as benzoquinone, oxirane, maleic acid, bismaleimide, diaminobenzophenone and terephthaldicarboxaldehyde to carry out a nucleophilic addition. Lin et al. disclosed the synthesis processes and applications of tri-functional curing agents, dopotriol [1] and dopo-ta [2] in 2005, and successfully obtained epoxy resins with flame retardancy and high glass transition temperature. However, the raw material, rosolic acid, used for synthesizing dopotriol in the references is too expensive to be cost-efficient in industrial applications. The present invention has successfully synthesized compound A (dopotriol) by reacting cheaper 4,4'-dihydroxy benzophenone (DHBP) and DOPO with phenol. Besides, the present invention also discloses the synthesis of DHBP, 4,4'-diamino benzophenone (DABP) and 4-amino-4'-hydroxy benzophenone (AHBP) derivatives.

REFERENCES

[1] C. H. Lin, S. X. Cai and C. H. Lin, "Flame-Retardant Epoxy Resins with High Glass-Transition Temperatures. II. Using a Novel Hexafunctional Curing Agent: 9,10-Dihydro-9-oxa-10-phosphaphenanthrene 10-yl-tris(4-aminophenyl)methane," *J. Polym. Sci. Polym. Chem.*, 2005, 43, 5971.

[2] S. X. Cai and C. H. Lin, "Flame-Retardant Epoxy Resins With High Tg from a Novel Tri-functional Curing Agent: Dopotriol," J. Polym. Sci. Polym. Chem., 2005, 43, 2862.

SUMMARY OF THE INVENTION

The present invention provides novel phosphorus-containing compounds having the following chemical formula:

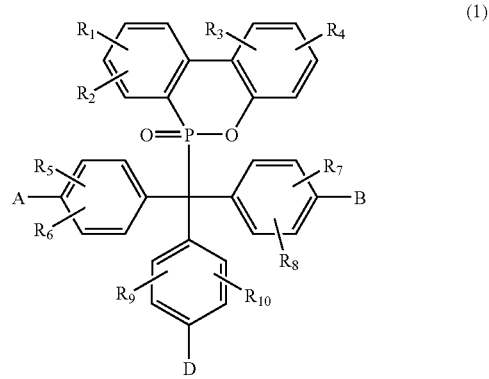

(1)

wherein $R_1$-$R_{10}$ are independently selected from the group consisting of H, $C_1$-$C_6$ alkyl, $C_1$-$C_6$ alkoxy, phenyl, nitro, phenoxy, $C_1$-$C_{10}$ halo-alkyl, $C_3$-$C_7$ cyclic alkyl, —$CF_3$, —$OCF_3$ and halogen;

A is —OH or —$NH_2$;

B is —OH or —$NH_2$;

D is selected from the group consisting of —OH, —$NH_2$, $C_1$-$C_6$ alkyl, $C_1$-$C_6$ alkoxy, $C_1$-$C_{10}$ halo-alkyl, $C_3$-$C_7$ cyclic alkyl, —$CF_3$, —$OCF_3$, halogen, —$NHR_1$, —NH(C=O)—$R_1$, —NH(O=C—O)—$R_1$, —NH(O=C—NH)—$R_1$,

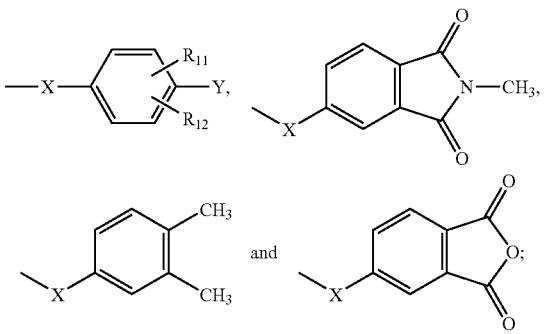

X is oxygen atom or —NH;

Y is selected from the group consisting of hydrogen, —$NO_2$, —OH, —$NH_2$, —COOH, $C_1$-$C_6$ alkyl, $C_1$-$C_6$ alkoxy, $C_3$-$C_7$ cyclic alkyl, —$CF_3$, —$OCF_3$ and halogen;

$R_{11}$-$R_{12}$ are independently selected from the group consisting of H, $C_1$-$C_6$ alkyl, $C_1$-$C_6$ alkoxy, phenyl, nitro, phenoxy, $C_1$-$C_{10}$ halo-alkyl, $C_3$-$C_7$ cyclic alkyl, —$CF_3$, —$OCF_3$ and halogen;

with the proviso that
(1) when D is —OH, and A and B are —$NH_2$,
at least one of $R_1$-$R_{10}$ is phenyl, nitro or phenoxy; or
(2) when A, B and D are —OH,
  (i) at least one of $R_1$-$R_{10}$ is $C_1$-$C_{10}$ halo-alkyl, —$CF_3$ or —$OCF_3$; or
  (ii) at least one of the substituent combinations, ($R_1$, $R_2$), ($R_3$, $R_4$), ($R_5$, $R_6$), ($R_7$, $R_8$) and ($R_9$, $R_{10}$), is different from the other combinations; or
(3) when D is selected from the group consisting of $C_1$-$C_6$ alkyl, $C_1$-$C_6$ alkoxy, $C_1$-$C_{10}$ halo-alkyl, $C_3$-$C_7$ cyclic alkyl, —$CF_3$, —$OCF_3$ and halogen, and A and B are —$NH_2$,
at least one of $R_1$-$R_{10}$ is phenyl, nitro or phenoxy; or
(4) when A, B and D are —$NH_2$,
  (i) at least one of $R_1$-$R_{10}$ is phenyl, nitro or phenoxy and at least one of the substituent combinations, ($R_1$, $R_2$), ($R_3$, $R_4$), ($R_5$, $R_6$), ($R_7$, $R_8$) and ($R_9$, $R_{10}$), is different from the other combinations; or
  (ii) at least one of $R_1$-$R_{10}$ is phenyl, nitro or phenoxy and at least one of $R_1$-$R_{10}$ is $C_1$-$C_{10}$ halo-alkyl, —$CF_3$ or —$OCF_3$.

The present invention also provides a process of preparing the compound of formula (1), which includes reacting an organophosphorous compound of formula (2) and a compound of formula (3) with a compound of formula (4) in the presence of an acid catalyst to form the compound of formula (1), wherein $R_1$-$R_{10}$, A, B and D are defined as above;

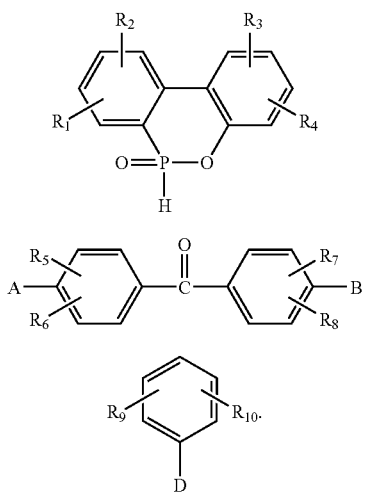

The present invention also provides a curing agent comprising the compound of formula (1) or a mixture thereof. The present invention also provides a flame resistant epoxy resin comprising an epoxy resin and the curing agent described above and the process for preparing the same.

DETAILED DESCRIPTION OF THE INVENTION

Figure 1A:
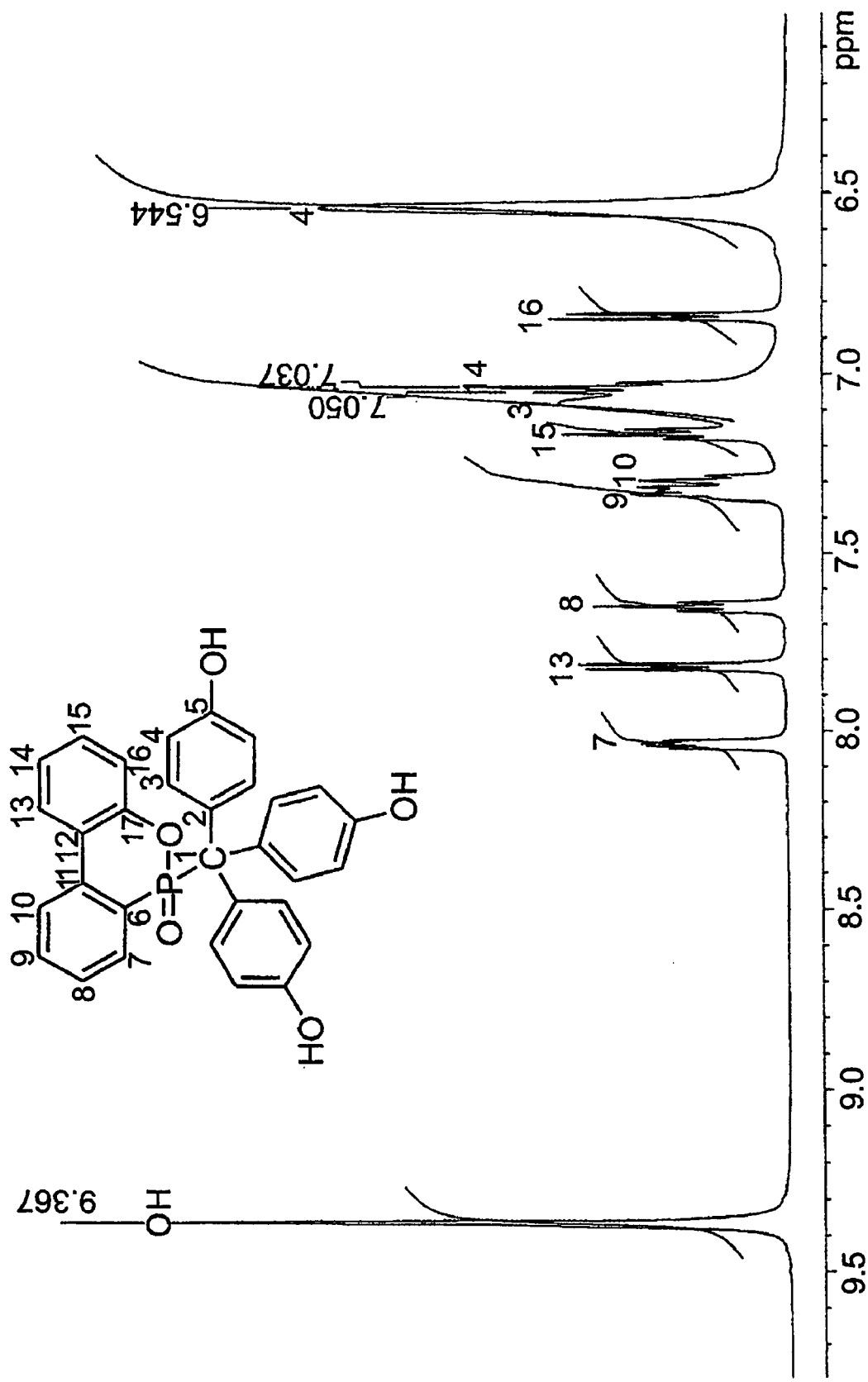
FIGS. 1A and 1B show $^1$H and $^{13}$C NMR spectra of compound A.

The present invention is directed to a series of novel phosphorus-containing compounds, which can be used as curing agents for epoxy resins and further used in the preparation of epoxy resins with flame resistance.

The present invention provides phosphorus-containing compounds having the following chemical formula:

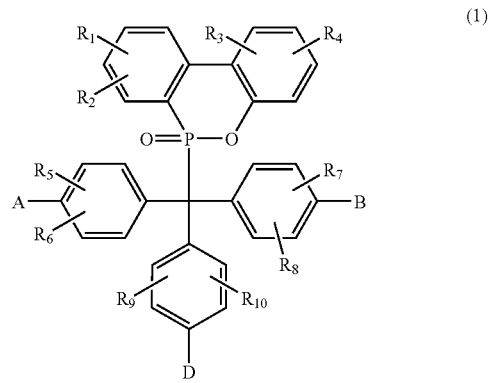

(1)

wherein
$R_1$-$R_{10}$ are independently selected from the group consisting of H, $C_1$-$C_6$ alkyl, $C_1$-$C_6$ alkoxy, phenyl, nitro, phenoxy, $C_1$-$C_{10}$ halo-alkyl, $C_3$-$C_7$ cyclic alkyl, —$CF_3$, —$OCF_3$ and halogen;
A is —OH or —$NH_2$;
B is —OH or —$NH_2$;
D is selected from the group consisting of —OH, —$NH_2$, $C_1$-$C_6$ alkyl, $C_1$-$C_6$ alkoxy, $C_1$-$C_{10}$ halo-alkyl, $C_3$-$C_7$ cyclic alkyl, —$CF_3$, —$OCF_3$, halogen, —$NHR_1$, —NH(C=O)—$R_1$, —NH(O=C—O)—$R_1$, —NH(O=C—NH)—$R_1$,

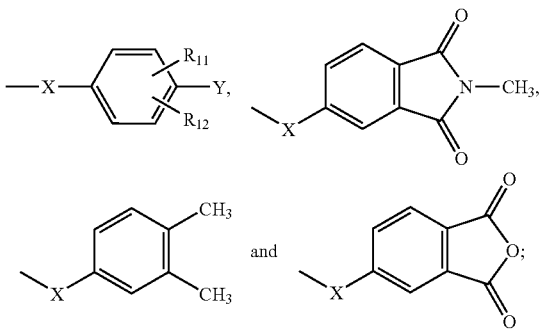

X is oxygen atom or —NH;
Y is selected from the group consisting of hydrogen, —$NO_2$, —OH, —$NH_2$, —COOH, $C_1$-$C_6$ alkyl, $C_1$-$C_6$ alkoxy, $C_3$-$C_7$ cyclic alkyl, —$CF_3$, —$OCF_3$ and halogen;
$R_{11}$-$R_{12}$ are independently selected from the group consisting of H, $C_1$-$C_6$ alkyl, $C_1$-$C_6$ alkoxy, phenyl, nitro, phenoxy, $C_1$-$C_{10}$ halo-alkyl, $C_3$-$C_7$ cyclic alkyl, —$CF_3$, —$OCF_3$ and halogen;

with the proviso that
(1) when D is —OH, and A and B are —NH$_2$,
at least one of R$_1$-R$_{10}$ is phenyl, nitro or phenoxy; or
(2) when A, B and D are —OH,
(i) at least one of R$_1$-R$_{10}$ is C$_1$-C$_{10}$ halo-alkyl, —CF$_3$ or —OCF$_3$; or
(ii) at least one of the substituent combinations, (R$_1$, R$_2$), (R$_3$, R$_4$), (R$_5$, R$_6$), (R$_7$, R$_8$) and (R$_9$, R$_{10}$), is different from the other combinations; or
(3) when D is selected from the group consisting of C$_1$-C$_6$ alkyl, C$_1$-C$_6$ alkoxy, C$_1$-C$_{10}$ halo-alkyl, C$_3$-C$_7$ cyclic alkyl, —CF$_3$, —OCF$_3$ and halogen, and A and B are —NH$_2$,
at least one of R$_1$-R$_{10}$ is phenyl, nitro or phenoxy; or
(4) when A, B and D are —NH$_2$,
(i) at least one of R$_1$-R$_{10}$ is phenyl, nitro or phenoxy and at least one of the substituent combinations, (R$_1$, R$_2$), (R$_3$, R$_4$), (R$_5$, R$_6$), (R$_7$, R$_8$) and (R$_9$, R$_{10}$), is different from the other combinations; or
(ii) at least one of R$_1$-R$_{10}$ is phenyl, nitro or phenoxy and at least one of R$_1$-R$_{10}$ is C$_1$-C$_{10}$ halo-alkyl, —CF$_3$ or —OCF$_3$.

When A, B and D are —OH, R$_1$-R$_9$ are independently hydrogen, and R$_{10}$ is —CH$_3$, the compound of formula (1) can have a structural formula of

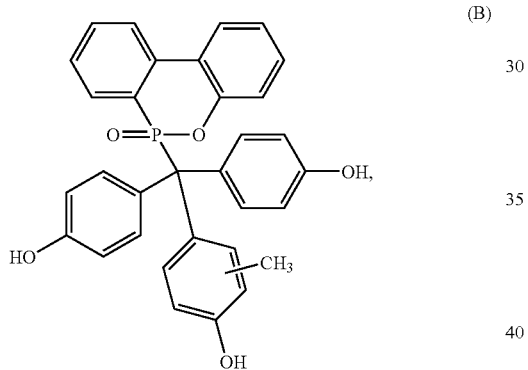

(B)

wherein in an embodiment R$_{10}$ is attached to the carbon at position 3 on the benzene ring.

When A, B and D are —OH, R$_1$-R$_8$ are independently hydrogen, and R$_9$ and R$_{10}$ are —CH$_3$, the compound of formula (1) can have a structural formula of

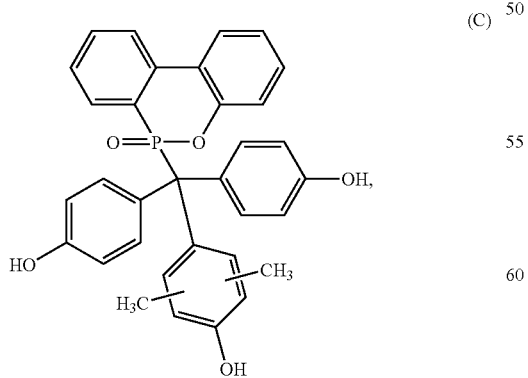

(C)

wherein in an embodiment R$_9$ and R$_{10}$ are attached to the carbons at positions 3 and 5 on the benzene ring.

When A and B are —OH, D is —NH$_2$, and R$_1$-R$_{10}$ are independently hydrogen, the compound of formula (1) can have a structural formula of

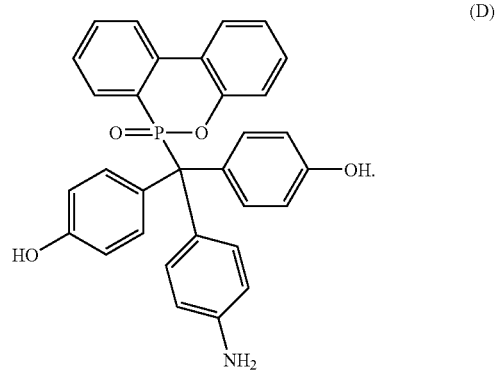

(D)

When A and B are —OH, D is —NH$_2$, R$_1$-R$_9$ are independently hydrogen, and R$_{10}$ is —CH$_3$, the compound of formula (1) can have a structural formula of

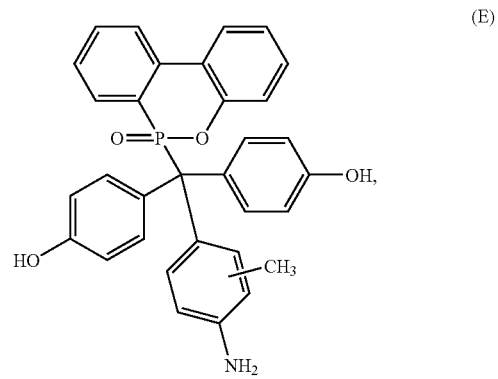

(E)

wherein in an embodiment R$_{10}$ is attached to the carbon at position 3 on the benzene ring.

When A and B are —OH, D is —NH$_2$, R$_1$-R$_8$ are independently hydrogen, and R$_9$ and R$_{10}$ are —CH$_3$, the compound of formula (1) can have a structural formula of

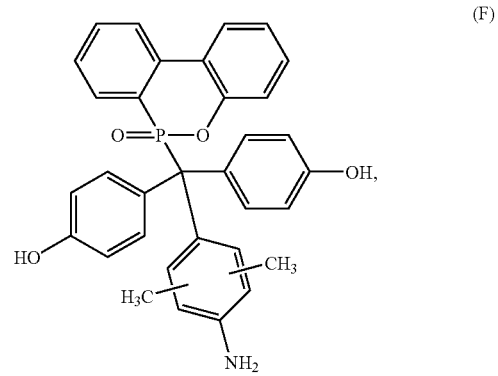

(F)

wherein in an embodiment R$_9$ and R$_{10}$ are attached to the carbons at positions 3 and 5 on the benzene ring.

The present invention provides a process of preparing the compound of formula (1), which includes reacting an organophosphorous compound of formula (2) and a compound of formula (3) with a compound of formula (4) in the presence of an acid catalyst to form the compound of formula (1), wherein $R_1$-$R_{10}$, A, B and D are defined as above;

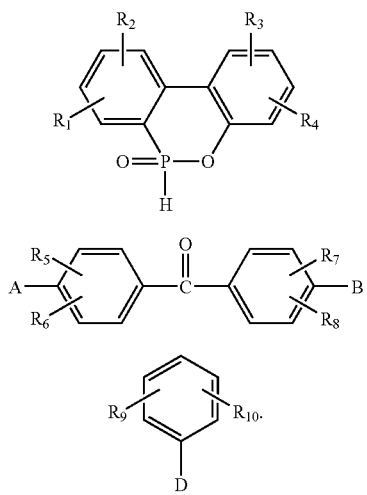

In an embodiment of the process described above, when A, B and D are —OH and $R_1$-$R_{10}$ are hydrogen, 9,10-dihydro-9-oxa-10-phosphaphenanthrene-10-oxide (DOPO) of formula (2) and 4,4'-dihydroxy benzophenone (DHBP) of formula (3) are reacted with phenol of formula (4) in the presence of an acid catalyst to form the compound of formula (A)

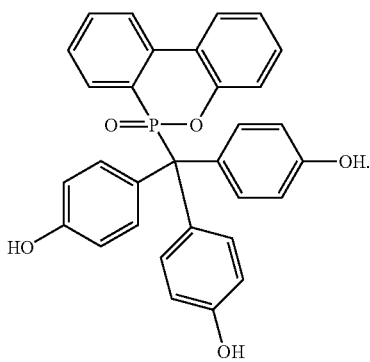

In an embodiment of the process described above, when A, B and D are —OH, $R_1$-$R_9$ are hydrogen, and $R_{10}$ is —CH$_3$, 9,10-dihydro-9-oxa-10-phosphaphenanthrene-10-oxide (DOPO) of formula (2) and 4,4'-dihydroxy benzophenone (DHBP) of formula (3) are reacted with 2-cresol of formula (4) in the presence of an acid catalyst to form the compound of formula (B).

In an embodiment of the process described above, when A, B and D are —OH, $R_1$-$R_8$ are hydrogen, and $R_9$ and $R_{10}$ are —CH$_3$, 9,10-dihydro-9-oxa-10-phosphaphenanthrene-10-oxide (DOPO) of formula (2) and 4,4'-dihydroxy benzophenone (DHBP) of formula (3) are reacted with 2,6-dimethylphenol of formula (4) in the presence of an acid catalyst to form the compound of formula (C).

In an embodiment of the process described above, when A and B are —OH, D is —NH$_2$, and $R_1$-$R_{10}$ are hydrogen, 9,10-dihydro-9-oxa-10-phosphaphenanthrene-10-oxide (DOPO) of formula (2) and 4,4'-dihydroxy benzophenone (DHBP) of formula (3) are reacted with aniline of formula (4) in the presence of an acid catalyst to form the compound of formula (D).

In an embodiment of the process described above, when A and B are —OH, D is —NH$_2$, $R_1$-$R_9$ are hydrogen, and $R_{10}$ is —CH$_3$, 9,10-dihydro-9-oxa-10-phosphaphenanthrene-10-oxide (DOPO) of formula (2) and 4,4'-dihydroxy benzophenone (DHBP) of formula (3) are reacted with o-toluidine of formula (4) in the presence of an acid catalyst to form the compound of formula (E).

In an embodiment of the process described above, when A and B are —OH, D is —NH$_2$, $R_1$-$R_8$ are hydrogen, and $R_9$ and $R_{10}$ are —CH$_3$, 9,10-dihydro-9-oxa-10-phosphaphenanthrene-10-oxide (DOPO) of formula (2) and 4,4'-dihydroxy benzophenone (DHBP) of formula (3) are reacted with 2,6-dimethylaniline of formula (4) in the presence of an acid catalyst to form the compound of formula (F).

In an embodiment of the process described above, when A and B are —NH$_2$, D is —OH, and $R_1$-$R_{10}$ are hydrogen, 9,10-dihydro-9-oxa-10-phosphaphenanthrene-10-oxide (DOPO) of formula (2) and 4,4'-diamino benzophenone (DABP) of formula (3) are reacted with phenol of formula (4) in the presence of an acid catalyst to form the compound of formula (G)

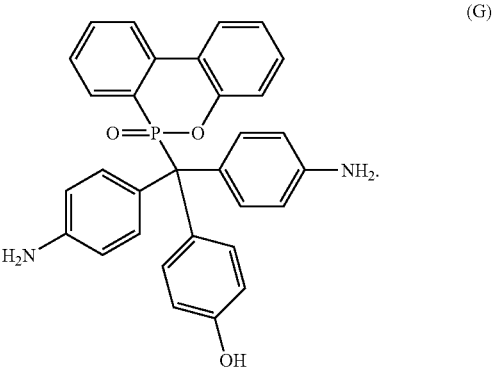

In an embodiment of the process described above, when A and B are —NH$_2$, D is —OH, $R_1$-$R_9$ are hydrogen, and $R_{10}$ is —CH$_3$, 9,10-dihydro-9-oxa-10-phosphaphenanthrene-10-oxide (DOPO) of formula (2) and 4,4'-diamino benzophenone (DABP) of formula (3) are reacted with 2-cresol of formula (4) in the presence of an acid catalyst to form the compound of formula (H)

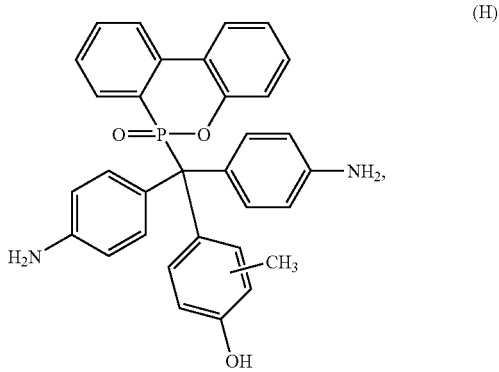

wherein in an embodiment $R_{10}$ is attached to the carbon at position 3 on the benzene ring.

In an embodiment of the process described above, when A and B are —NH$_2$, D is —OH, R$_1$-R$_8$ are hydrogen, and R$_9$ and R$_{10}$ are —CH$_3$, 9,10-dihydro-9-oxa-10-phosphaphenanthrene-10-oxide (DOPO) of formula (2) and 4,4'-diamino benzophenone (DABP) of formula (3) are reacted with 2,6-dimethylphenol of formula (4) in the presence of an acid catalyst to form the compound of formula (I)

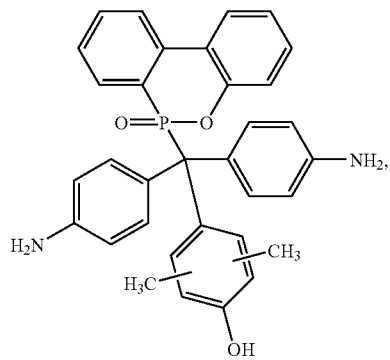

(I)

wherein in an embodiment R$_9$ and R$_{10}$ are attached to the carbons at positions 3 and 5 on the benzene ring.

In an embodiment of the process described above, when A, B and D are —NH$_2$ and R$_1$-R$_{10}$ are hydrogen, 9,10-dihydro-9-oxa-10-phosphaphenanthrene-10-oxide (DOPO) of formula (2) and 4,4'-diamino benzophenone (DABP) of formula (3) are reacted with aniline of formula (4) in the presence of an acid catalyst to form the compound of formula (J)

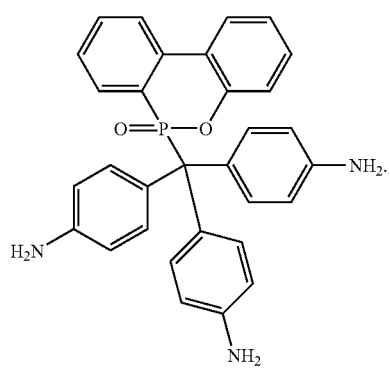

(J)

In an embodiment of the process described above, when A, B and D are —NH$_2$, R$_1$-R$_9$ are hydrogen, and R$_{10}$ is —CH$_3$, 9,10-dihydro-9-oxa-10-phosphaphenanthrene-10-oxide (DOPO) of formula (2) and 4,4'-diamino benzophenone (DABP) of formula (3) are reacted with o-toluidine of formula (4) in the presence of an acid catalyst to form the compound of formula (K)

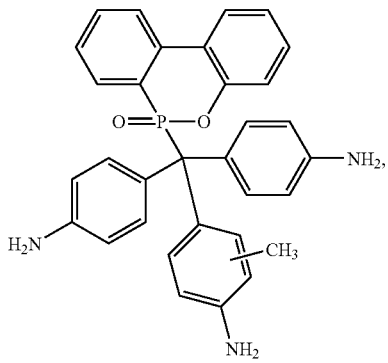

(K)

wherein in an embodiment R$_{10}$ is attached to the carbon at position 3 on the benzene ring.

In an embodiment of the process described above, when A, B and D are —NH$_2$, R$_1$-R$_8$ are hydrogen, and R$_9$ and R$_{10}$ are —CH$_3$, 9,10-dihydro-9-oxa-10-phosphaphenanthrene-10-oxide (DOPO) of formula (2) and 4,4'-diamino benzophenone (DABP) of formula (3) are reacted with 2,6-dimethylaniline of formula (4) in the presence of an acid catalyst to form the compound of formula (L)

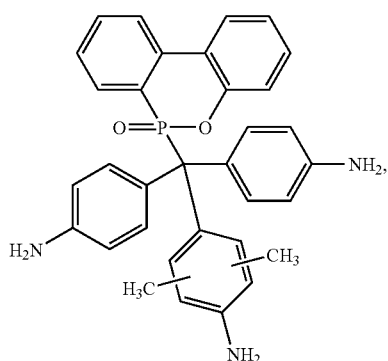

(L)

wherein in an embodiment R$_9$ and R$_{10}$ are attached to the carbons at positions 3 and 5 on the benzene ring.

In an embodiment of the process described above, when R$_1$-R$_{10}$ are hydrogen, A is —NH$_2$, and B and D are —OH, 9,10-dihydro-9-oxa-10-phosphaphenanthrene-10-oxide (DOPO) of formula (2) and 4-amino-4'-hydroxy benzophenone (AHBP) of formula (3) are reacted with phenol of formula (4) in the presence of an acid catalyst to form the compound of formula (D')

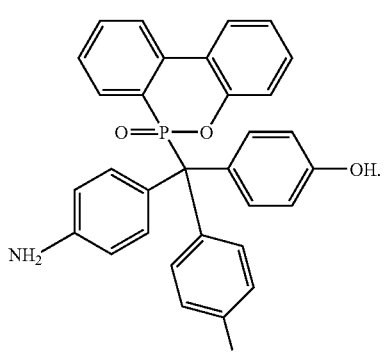

(D')

Due to the rotation of the chemical bond of carbon attached to phosphorus in this structure, the compound of formula (D') can be represented as the compound of formula (D).

In an embodiment of the process described above, when $R_1$-$R_{10}$ are hydrogen, A and D are —$NH_2$, and B is —OH, 9,10-dihydro-9-oxa-10-phosphaphenanthrene-10-oxide (DOPO) of formula (2) and 4-amino-4'-hydroxy benzophenone (AHBP) of formula (3) are reacted with aniline of formula (4) in the presence of an acid catalyst to form the compound of formula (G')

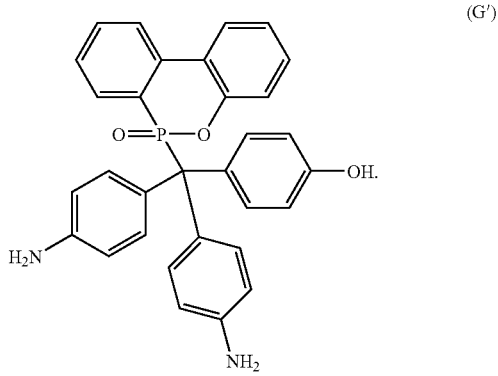

(G')

Similarly, due to the rotation of the chemical bond of carbon attached to phosphorus in this structure, the compound of formula (G') can be represented as the compound of formula (G).

The acid catalyst used in the process of the present invention is selected from the group consisting of protic acids and Lewis acids.

The acid catalyst used in the process of the present invention is selected from the group consisting of acetic acid, p-toluenesulfonic acid (PTSA), methanesulfonic acid, calmagite, sulfuric acid, orthanilic acid, 3-pyridinesulfonic acid, sulfanilic acid, hydrogen chloride (HCl), hydrogen bromide (HBr), hydrogen iodide (HI), hydrogen fluoride (HF), trifluoroacetic acid ($CF_3COOH$), nitric acid ($HNO_3$), phosphoric acid ($H_3PO_4$), aluminum chloride ($AlCl_3$), boron fluoride ($BF_3$), ferric bromide ($FeBr_3$), ferric chloride ($FeCl_3$), boron chloride ($BCl_3$), and titanium chloride ($TiCl_4$).

The amount of the acid catalyst used in the process described above is 0.1 wt %-30 wt % of the amount of the organophosphorous compound.

The present invention provides a curing agent comprising the compound of formula (1) or a mixture thereof.

The present invention provides a flame resistant epoxy resin comprising an epoxy resin and the curing agent described above, wherein the epoxy resin can be bisphenol A type epoxy resin (e.g., diglycidyl ether of bisphenol A, DGEBA) or o-cresol formaldehyde novolac epoxy resin (CNE).

The present invention provides a process of preparing the flame resistant epoxy resin, which includes uniformly mixing the epoxy resin and the curing agent described above in an equivalent proportion of 1:0.1 to 1:1 and curing to obtain the cured and flame resistant epoxy resin.

In an embodiment of the process of preparing the flame resistant epoxy resin as described above, the epoxy resin used is DGEBA and CNE.

The following embodiments are used to further illustrate the present invention, but are not intended to limit the scope of the present invention. Any modifications and changes made by those skilled in the art without departing from the spirit of the present invention will fall within the scope of the present invention.

Specific embodiments of the present invention described above can be represented by Scheme 1 and are illustrated below.

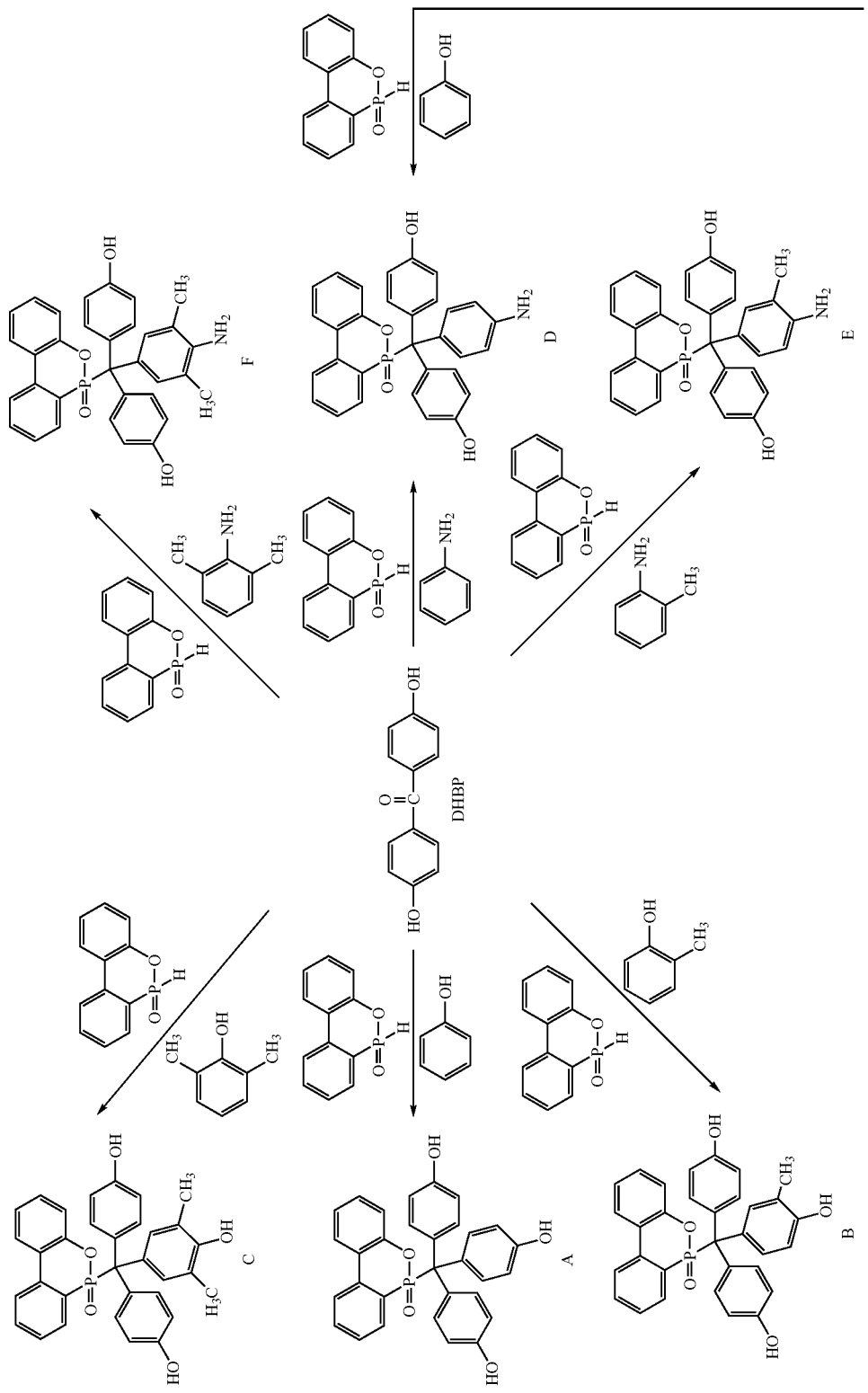
Scheme 1

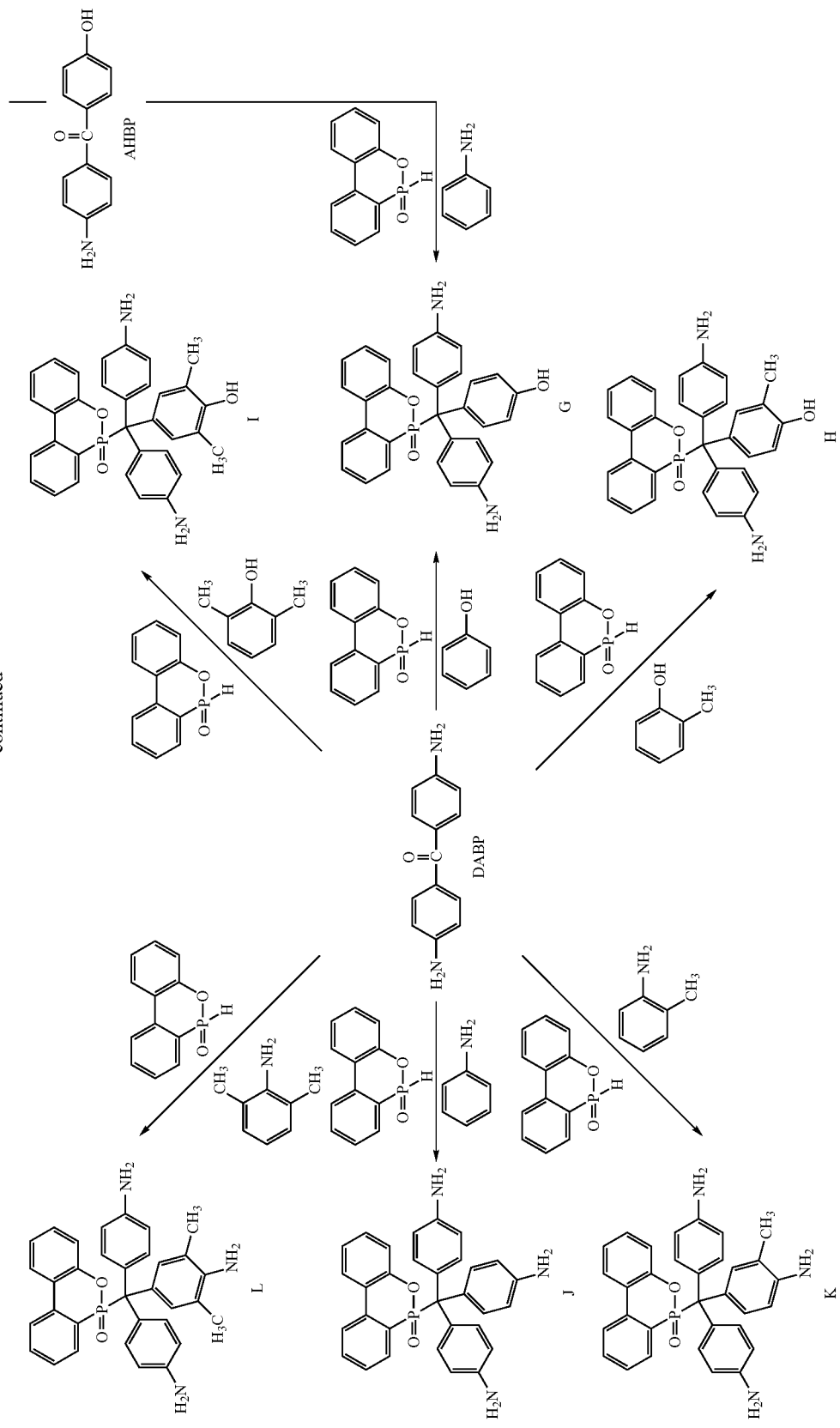

Example 1

Synthesis of Compound A

Compound A was synthesized by reacting DHBP and DOPO with phenol in the presence of an acid catalyst via the following steps. 26.75 g (0.125 mole) of 4,4'-dihydroxy benzophenone (DHBP), 27.00 g (0.125 mole) of 9,10-dihydro-9-oxa-10-phosphaphenanthrene 10-oxide (DOPO), 100 g of phenol and 1.10 g of sulfuric acid were added to a 1 L three-necked reactor equipped with a temperature indicator. The reaction temperature was raised to 130° C. and the reaction was continued for 12 hours. The resulting mixture was added dropwise to 500 ml of hot water and stirred to precipitate a product, i.e. compound A.

After suction filtration, the filter cake was washed with a large amount of hot water, separated by filtration and dried in a vacuum oven at 110° C. to obtain 54.50 g of compound A. The yield was 86% and M.P. was 294° C.

Figure 1B:
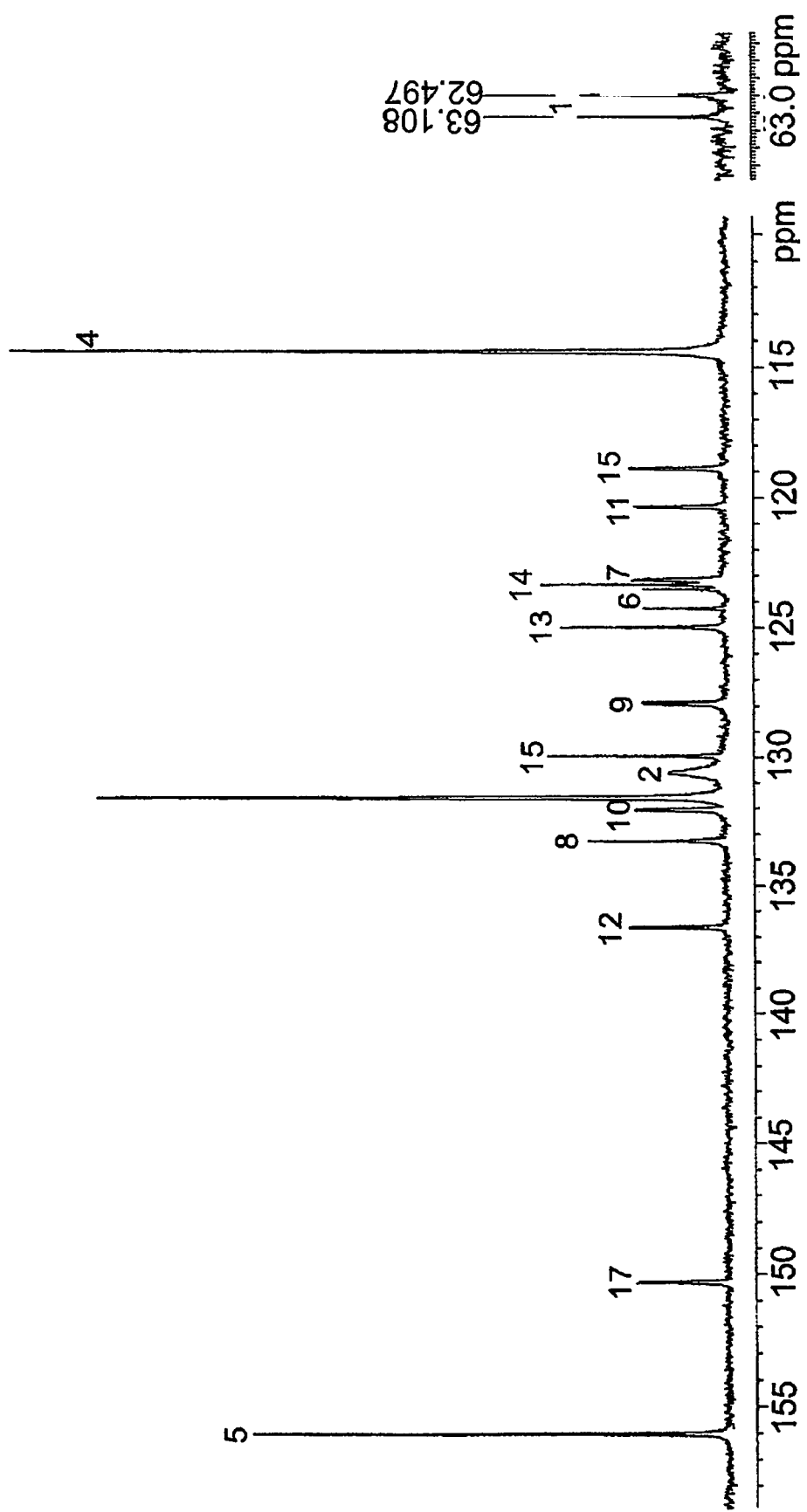
Figure 2:
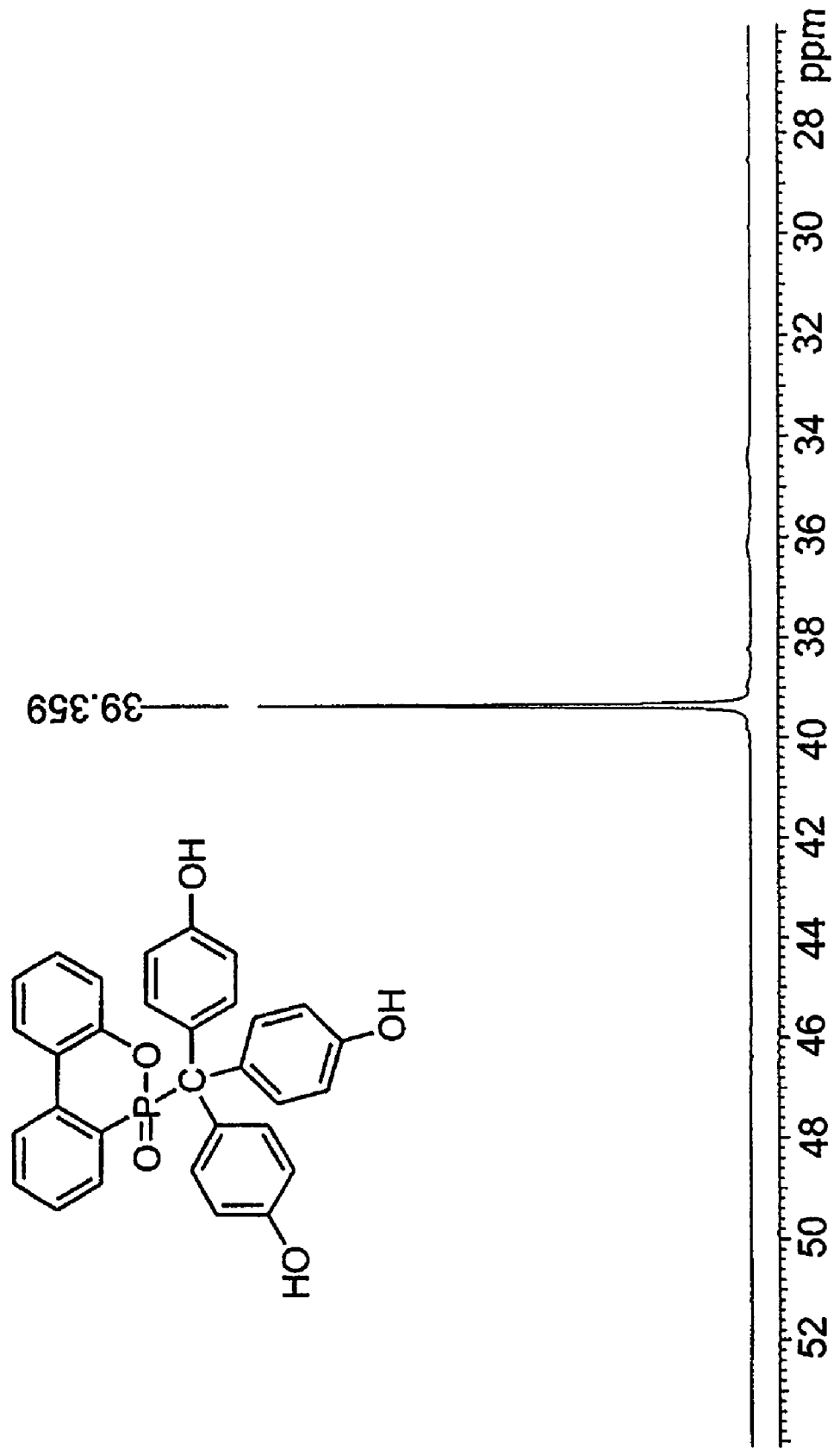
FIG. 2 is a $^{31}$P NMR spectrum of compound A.

The $^1$H NMR and $^{13}$C NMR spectra, and the $^{31}$P NMR spectrum of the compound A are shown in FIGS. 1A, 1B, and 2, respectively. The analysis results indicate that the resulting product is compound A.

Example 2

Synthesis of Compound B

Compound B was synthesized by reacting DHBP and DOPO with 2-cresol in the presence of an acid catalyst via the following steps. 21.40 g (0.1 mole) of DHBP, 21.60 g (0.1 mole) of DOPO, 100 g of 2-cresol and 1.10 g of sulfuric acid were added to a 1 L three-necked reactor equipped with a temperature indicator. The reaction temperature was raised to 130° C. and the reaction was continued for 12 hours. The resulting mixture was added dropwise to 100 ml of toluene and stirred to precipitate an orange viscous product. After removal of the toluene, the viscous product was dissolved with ethanol, and the product was precipitated by adding the ethanol solution dropwise to deionized water.

After filtration and separation, the filter cake was dried in a vacuum oven at 100° C. to obtain 35.00 g of orange solid compound B. The yield was 67% and M.P. was 284° C.

Example 3

Synthesis of Compound C

Compound C was synthesized by reacting DHBP and DOPO with 2,6-dimethylphenol in the presence of an acid catalyst via the following steps. 21.40 g (0.1 mole) of DHBP, 21.60 g (0.1 mole) of DOPO, 100 g of 2,6-dimethylphenol and 1.1 g of sulfuric acid were added to a 1 L three-necked reactor equipped with a temperature indicator. The reaction temperature was raised to 130° C. and the reaction was continued for 12 hours. The resulting mixture was added dropwise to 100 ml of toluene and stirred to precipitate an orange viscous product. After removal of the toluene, the viscous product was dissolved with ethanol, and the product was precipitated by adding the ethanol solution dropwise to deionized water.

After filtration and separation, the filter cake was dried in a vacuum oven at 100° C. to obtain 40.00 g of organe solid compound C. The yield was 75% and M.P. was 291° C.

Example 4

Synthesis of Compound D

Compound D was synthesized by reacting DHBP and DOPO with aniline in the presence of an acid catalyst via the following steps. 21.40 g (0.1 mole) of DHBP, 21.60 g (0.1 mole) of DOPO, 100 g of aniline and 4.30 g of p-toluenesulfonic acid (PTSA) were added to a 1 L three-necked reactor equipped with a temperature indicator. The reaction temperature was raised to 130° C. and the reaction was continued for 12 hours. The resulting mixture was added dropwise to 100 ml of acetonitrile and stirred to precipitate a yellow solid, i.e. compound D.

After filtration and separation, the product was washed with heated acetonitrile. After suction filtration, the filter cake was dried in a vacuum oven at 100° C. to obtain 34.00 g of white solid compound D. The yield was 68% and M.P. was 300° C.

Figure 3A:
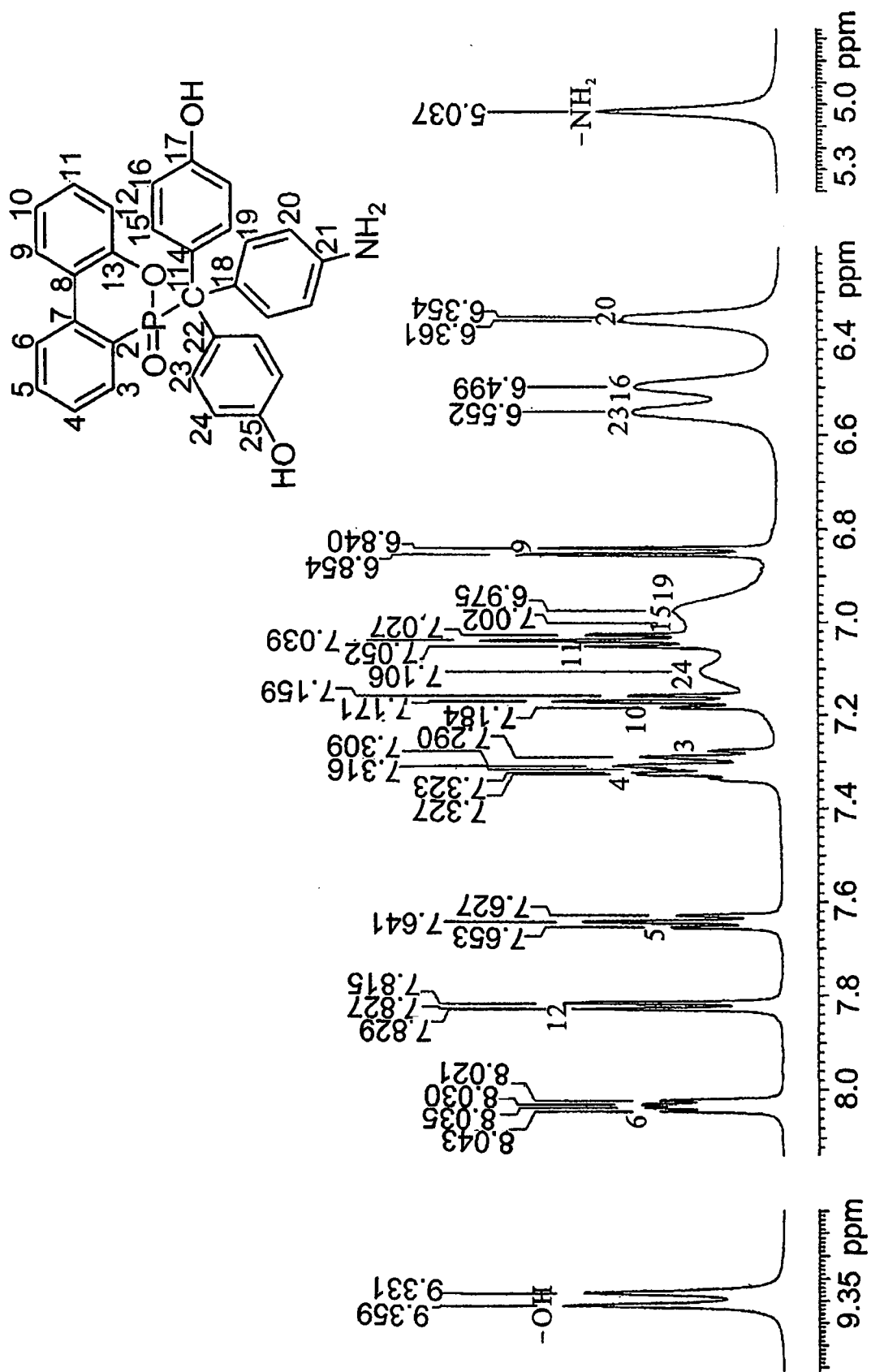
FIGS. 3A and 3B show $^1$H and $^{13}$C NMR spectra of compound D.
Figure 3B:
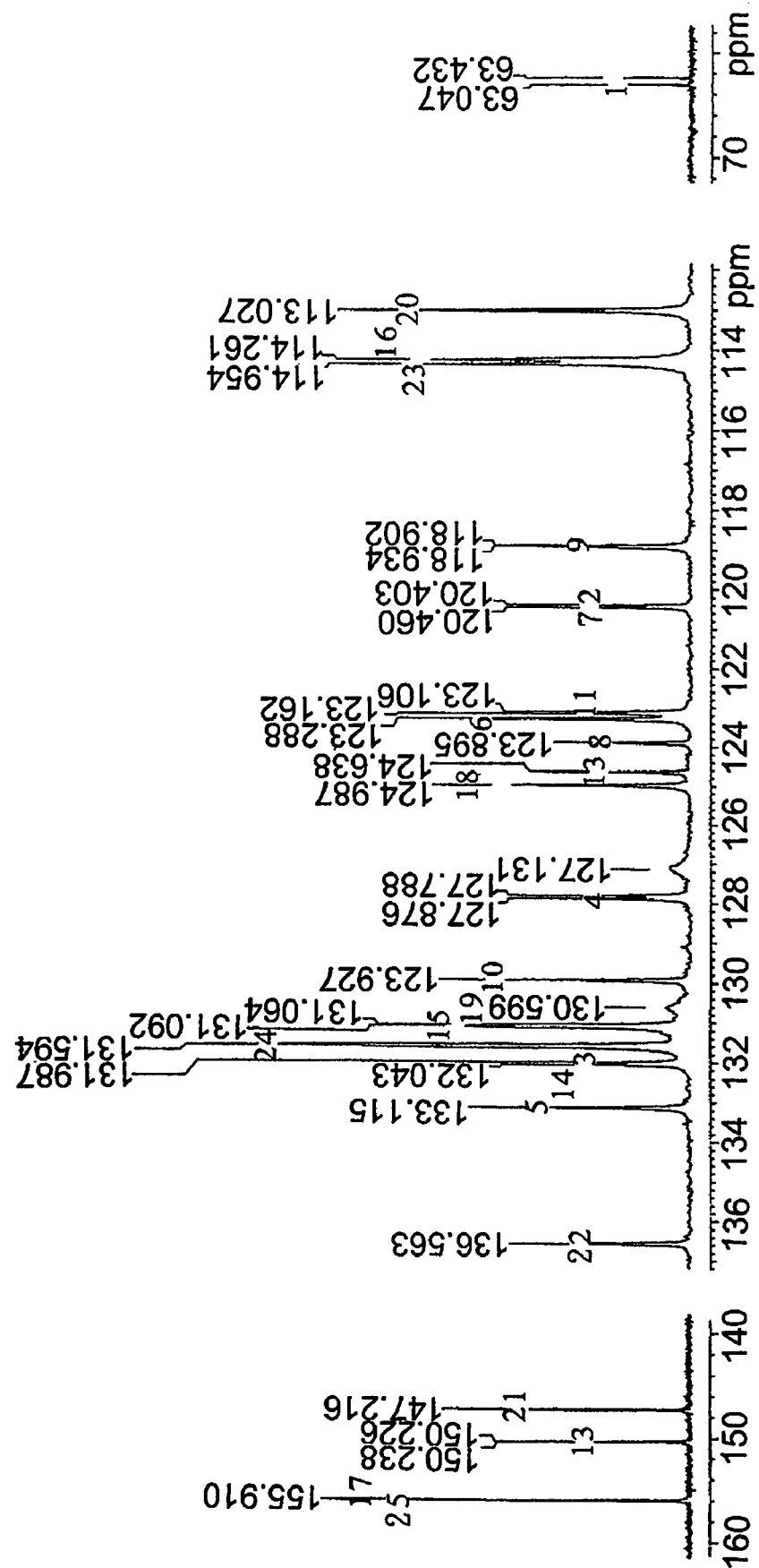
Figure 4:
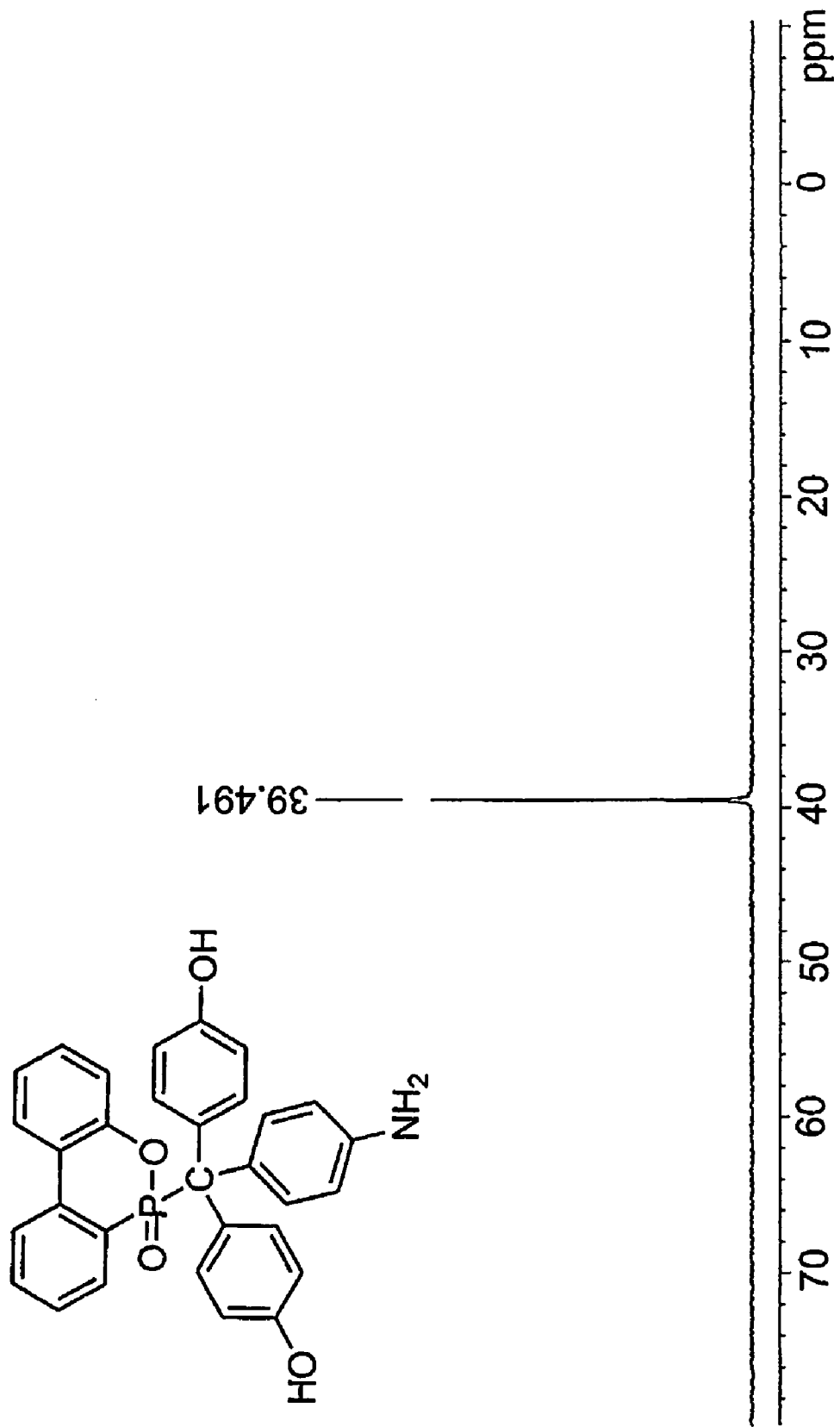
FIG. 4 is a $^{31}$P NMR spectrum of compound D.

The $^1$H NMR and $^{13}$C NMR spectra and the $^{31}$P NMR spectrum of compound D are shown in FIGS. 3A, 3B, and 4, respectively.

Example 5

Synthesis of Compound E

Compound E was synthesized by reacting DHBP and DOPO with o-toluidine in the presence of an acid catalyst via the following steps. 21.40 g (0.1 mole) of DHBP, 21.60 g (0.1 mole) of DOPO, 100 g of o-toluidine and 4.30 g of p-toluenesulfonic acid (PTSA) were added to a 1 L three-necked reactor equipped with a temperature indicator. The reaction temperature was raised to 130° C. and the reaction was continued for 12 hours. The resulting mixture was added dropwise to 100 ml of toluene and stirred to precipitate a brown viscous product. After removal of the toluene, the viscous product was dissolved with ethanol, and the product was precipitated by adding the ethanol solution dropwise to deionized water.

After filtration and separation, the product was washed with heated acetonitrile. After suction filtration, the filter cake was dried in a vacuum oven at 100° C. to give 37.00 g of light purple solid compound E. The yield was 72% and M.P. was 283° C.

Example 6

Synthesis of Compound F

Compound F was synthesized by reacting DHBP and DOPO with 2,6-dimethylaniline in the presence of an acid catalyst via the following steps. 21.40 g (0.1 mole) of DHBP, 21.60 g (0.1 mole) of DOPO, 100 g of 2,6-dimethylaniline and 4.30 g of p-toluenesulfonic acid (PTSA) were added to a 1 L three-necked reactor equipped with a temperature indicator. The reaction temperature was raised to 130° C. and the reaction was continued for 12 hours. The resulting mixture was added dropwise to 100 ml of toluene and stirred to precipitate a brown viscous product. After removal of the toluene, the viscous product was dissolved with ethanol, and the product was precipitated by adding the ethanol solution dropwise to deionized water.

After filtration and separation, the product was washed with heated acetonitrile. After suction filtration, the filter cake

Example 7

Synthesis of Compound G

Compound G was synthesized by reacting DABP and DOPO with phenol in the presence of an acid catalyst via the following steps. 26.53 g (0.125 mole) of DABP, 27.00 g (0.125 mole) of DOPO, 25.00 g of phenol and 1.10 g of sulfuric acid were added to a 1 L three-necked reactor equipped with a temperature indicator. The reaction temperature was raised to 130° C. and the reaction was continued for 12 hours. The resulting mixture was added dropwise to 500 ml of hot water and stirred to precipitate an orange solid, i.e. compound G.

After filtration and separation, the filter cake was then washed with a large amount of hot water. After suction filtration, the cake was dried in a vacuum oven at 110° C. to give 45.40 g of compound G. The yield was 72% and M.P. was 298° C.

Example 8

Synthesis of Compound H

Compound H was synthesized by reacting DABP and DOPO with 2-cresol in the presence of an acid catalyst via the following steps. 26.53 g (0.125 mole) of DABP, 27.00 g (0.125 mole) of DOPO, 100 g of 2-cresol and 1.10 g of sulfuric acid were added to a 1 L three-necked reactor equipped with a temperature indicator. The reaction temperature was raised to 130° C. and the reaction was continued for 12 hours. The resulting mixture was added dropwise to 100 ml of toluene and stirred to precipitate a brown viscous product. After removal of the toluene, the viscous product was dissolved with ethanol, and the product was precipitated by adding the ethanol solution dropwise to deionized water.

After filtration and separation, the filter cake was dried in a vacuum oven at 100° C. to give 33.70 g of pink solid compound H. The yield was 65% and M.P. was 287° C.

Example 9

Synthesis of Compound I

Compound I was synthesized by reacting DABP and DOPO with 2,6-dimethylphenol in the presence of an acid catalyst via the following steps. 26.53 g (0.125 mole) of DABP, 27.00 g (0.125 mole) of DOPO, 100 g of 2,6-dimethylphenol and 1.10 g of sulfuric acid were added to a 1 L three-necked reactor equipped with a temperature indicator. The reaction temperature was raised to 130° C. and the reaction was continued for 12 hours. The resulting mixture was added dropwise to 100 ml of toluene and stirred to precipitate a brown viscous product. After removal of the toluene, the viscous product was dissolved with ethanol, and the product was precipitated by adding the ethanol solution dropwise to deionized water.

After filtration and separation, the filter cake was dried in a vacuum oven at 100° C. to give 40.40 g of purple solid compound I. The yield was 76% and M.P. was 293° C.

was dried in a vacuum oven at 100° C. to give 27.00 g of light yellow solid compound F. The yield was 50% and M.P. was 292° C.

Example 10

Synthesis of Compound J

Compound J was synthesized by reacting DABP and DOPO with aniline in the presence of an acid catalyst via the following steps. 26.53 g (0.125 mole) of DABP, 27.00 g (0.125 mole) of DOPO, 100.00 g of aniline and 4.30 g of PTSA were added to a 1 L three-necked reactor equipped with a temperature indicator. The reaction temperature was raised to 130° C. and the reaction was continued for 12 hours. The resulting mixture was added dropwise to 100 ml of acetonitrile and stirred to precipitate a light purple solid, i.e. compound J.

After filtration and separation, the product was washed with heated acetonitrile. After suction filtration, the product was dried in a vacuum oven at 100° C. to give 29.00 g of compound J. The yield was 57% and M.P. was 330° C.

Example 11

Synthesis of Compound K

Compound K was synthesized by reacting DABP and DOPO with o-toluidine in the presence of an acid catalyst via the following steps. 26.53 g (0.125 mole) of DABP, 27.00 g (0.125 mole) of DOPO, 100.00 g of o-toluidine and 4.30 g of PTSA were added to a 1 L three-necked reactor equipped with a temperature indicator. The reaction temperature was raised to 130° C. and the reaction was continued for 12 hours. The resulting mixture was added dropwise to 100 ml of toluene and stirred to precipitate a brown viscous product. After removal of the toluene, the viscous product was dissolved with ethanol, and the product was precipitated by adding the ethanol solution dropwise to deionized water.

After filtration and separation, the product was washed with heated acetonitrile. After suction filtration, the product was dried in a vacuum oven at 100° C. to give 32.00 g of compound K. The yield was 62% and M.P. was 323° C.

Example 12

Synthesis of Compound L

Compound L was synthesized by reacting DABP and DOPO with 2,6-dimethylaniline in the presence of an acid catalyst via the following steps. 26.53 g (0.1 mole) of DABP, 21.60 g (0.1 mole) of DOPO, 100.00 g of 2,6-dimethylaniline and 4.30 g of PTSA were added to a 1 L three-necked reactor equipped with a temperature indicator. The reaction temperature was raised to 130° C. and the reaction was continued for 12 hours. The resulting mixture was added dropwise to 100 ml of toluene and stirred to precipitate a brown viscous product. After removal of the toluene, the viscous product was dissolved with ethanol, and the product was precipitated by adding the ethanol solution dropwise to deionized water.

After filtration and separation, the product was washed with heated acetonitrile. After suction filtration, the product was dried in a vacuum oven at 100° C. to give 27.60 g of compound L. The yield was 52% and M.P. was 329° C.

Example 13

Synthesis of Compound D

Compound D was also synthesized by reacting AHBP and DOPO with phenol in the presence of an acid catalyst via the following steps. 21.30 g (0.1 mole) of AHBP, 21.60 g (0.1 mole) of DOPO, 100.00 g of phenol and 0.86 g of sulfuric acid were added to a 1 L three-necked reactor equipped with a temperature indicator. The reaction temperature was raised to 130° C. and the reaction was continued for 12 hours. The resulting mixture was added dropwise to 100 ml of acetonitrile and stirred to precipitate a yellow solid, i.e. compound D.

After suction filtration, the filter cake was washed with heated acetonitrile. After filtration and separation, the filter cake was dried in a vacuum oven at 100° C. to give 30.00 g of white solid compound D. The yield was 60% and M.P. was 300° C.

The $^1$H and $^{13}$C NMR spectra of the product in DMSO-D6 solution completely conform to those shown in FIGS. 3A and 3B, indicating that the product is indeed compound D.

Example 14

Synthesis of Compound G

Compound G was also synthesized by reacting AHBP and DOPO with aniline in the presence of an acid catalyst via the following steps. 21.30 g (0.1 mole) of AHBP, 21.60 g (0.1 mole) of DOPO, 25.00 g of aniline and 4.32 g of $H_2SO_4$ were added to a 1 L three-necked reactor equipped with a temperature indicator. The reaction temperature was raised to 130° C. and the reaction was continued for 12 hours. The resulting mixture was added dropwise to 500 ml of hot water and stirred to precipitate an orange solid, i.e. compound G.

After filtration and separation, the filter cake was washed with a large amount of hot water. After suction filtration, the filter cake was dried in a vacuum oven at 110° C. to give 41.62 g of compound G. The yield was 66% and M.P. was 298° C.

Example 15

Preparation and Analysis of the Flame Resistant Epoxy Resin

Compound A, compound B, and compound E obtained from the synthesis examples described above were used as curing agents for epoxy resins diglycidyl ether of bisphenol A (DGEBA) and o-cresol formaldehyde novolac epoxy resin (CNE). They were uniformly mixed in an equivalent proportion of 1:1, and cured to give the cured flame resistant epoxy resins. The effects of the curing agents were compared in the following analysis and test. The samples are as shown in Table 1:

TABLE 1

Samples of cured products

| Sample of cured product | Epoxy resin | Curing agent | Catalyst |
|---|---|---|---|
| A-DGEBA | DGEBA | A | None |
| A-DGEBA(I) | DGEBA | A | 0.2 wt % imidazole |
| B-DGEBA | DGEBA | D | None |
| B-DGEBA(I) | DGEBA | D | 0.2 wt % imidazole |
| E-DGEBA | DGEBA | J | None |
| E-DGEBA(I) | DGEBA | J | 0.2 wt % imidazole |

TABLE 1-continued

Samples of cured products

| Sample of cured product | Epoxy resin | Curing agent | Catalyst |
|---|---|---|---|
| B-CNE | CNE | D | None |
| B-CNE(I) | CNE | D | 0.2 wt % imidazole |
| E-CNE | CNE | J | None |
| E-CNE(I) | CNE | J | 0.2 wt % imidazole |

Thermal Property Analysis

Figure 5:
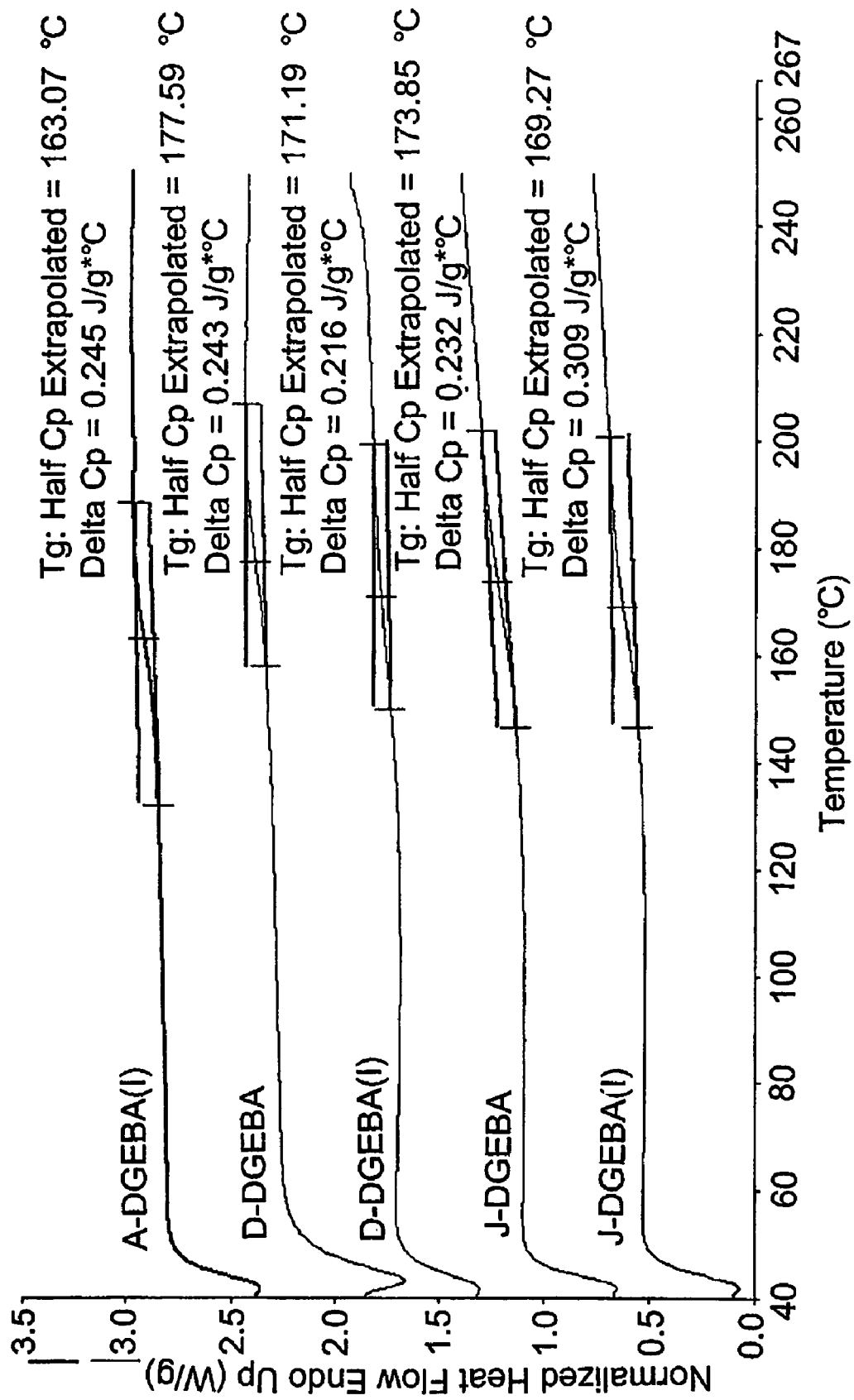
FIG. 5 shows DSC curves of DGEBA-series cured products.
Figure 6:
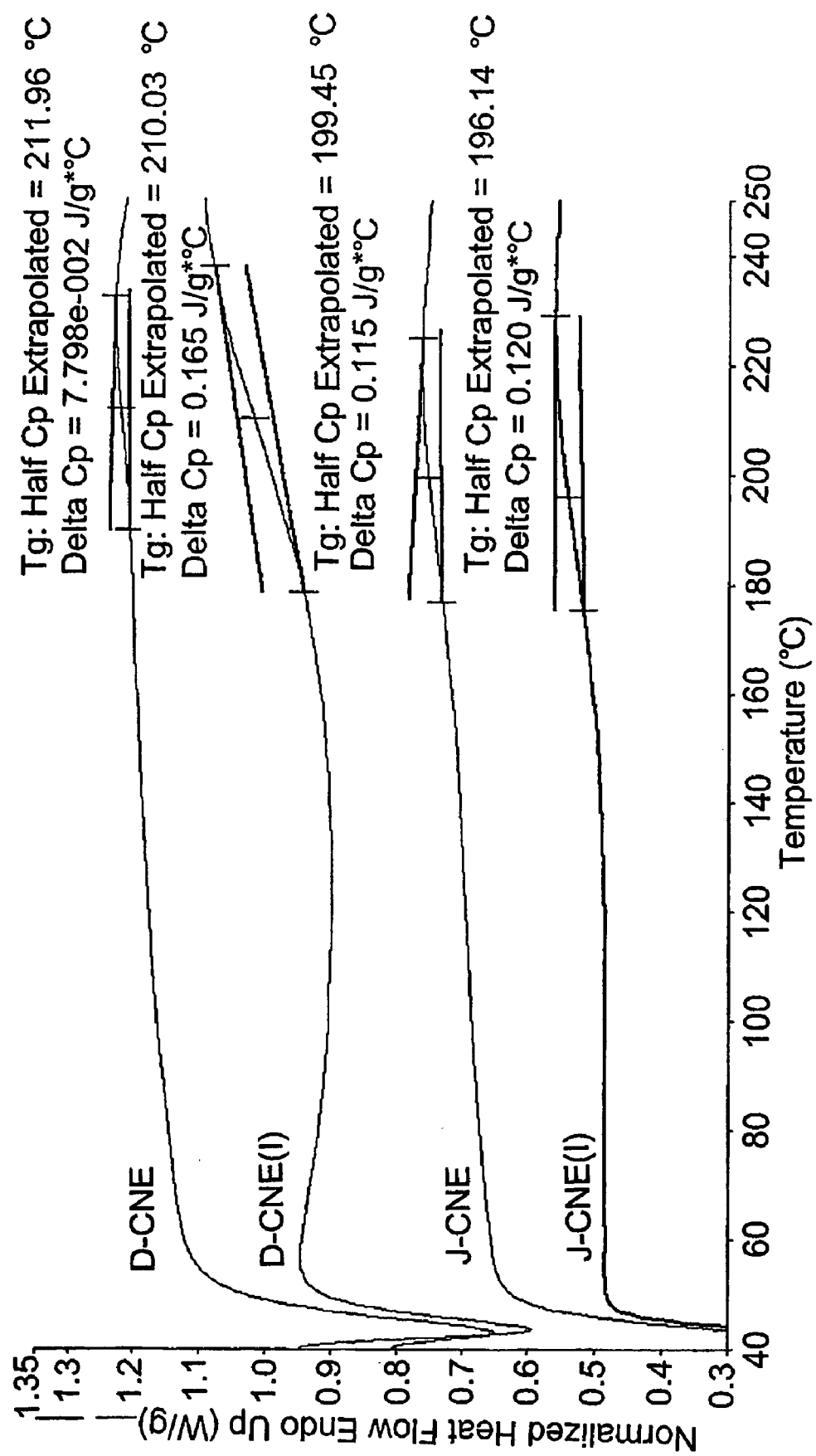
FIG. 6 shows DSC curves of CNE-series cured products.

FIG. 5 shows an overlap of glass transition temperature curves of the cured DGEBA after DGEBA was uniformly mixed with different curing agents. FIG. 6 shows an overlap of glass transition temperature curves of the cured CNE after CNE was uniformly mixed with different curing agents. Table 2 and Table 3 show the glass transition temperatures, which were measured by DSC, of the epoxy resin mixtures described above at different curing temperatures. It can be found that the glass transition temperatures of the cured epoxy resins are in the following order: B-DGEBA>J-DGEBA>D-DGEBA(I)>J-DGEBA(I)>A-DGEBA(I). The results show that addition of the curing-promoting agent (imidazole) has little influence on the glass transition temperatures of the cured epoxy resins. Furthermore, the cured epoxy resins with compound D and compound J as curing agents have higher glass transition temperatures. This is because compound D and compound J provide more cross-linking sites to increase the crosslink density. Therefore, the cured epoxy resins have higher glass transition temperatures.

Additionally, a comparison shows that the glass transition temperatures of the cured epoxy resins are in the following order: D-CNE>D-CNE(I)>J-CNE>J-CNE(I). The analysis results show that whether the curing-promoting agent is added has little influence. The glass transition temperatures of the D-series cured epoxy resins are higher than those of the J-series cured epoxy resins. This is because compound J may be influenced by the steric hindrance during the cross-linking, which blocks the extension of the cross-linked structure and thereby lowers the glass transition temperature. The results in Table 2 show that the A- and J-series cured epoxy resins have the highest glass transition temperatures at the curing temperature of 220° C. and have slight cleavage phenomenon at the curing temperature of 240° C. which lowers the glass transition temperatures. D-DGEBA has the highest glass transition temperature at the curing temperature of 180° C. D-DGEBA(I) can achieve the highest glass transition temperature at the curing temperature of 140° C. due to the addition of the curing-promoting agent. The analysis results show that the D-series cured epoxy resins have a faster curing rate than the A- and J-series cured epoxy resins. The D-series epoxy resins can achieve the highest glass transition temperature at a lower curing temperature. Table 3 also shows that not only the D-CNE(I) can achieve the highest glass transition temperature at the curing temperature of 220° C., but also the others can achieve the highest glass transition temperatures at the curing temperature of 240° C.

TABLE 2

DSC glass transition temperatures at different curing temperatures
Glass transition temperature after curing for 2 hours at different curing temperatures, Tg(° C.)[b]

| Sample | 120° C. | 140° C. | 160° C. | 180° C. | 200° C. | 220° C. | 240° C. |
|---|---|---|---|---|---|---|---|
| A-DGEBA(I)[a] | — | — | — | 135 | 151 | 163 | 157 |
| A-DGEBA(I)[c] | — | — | — | — | 156 | — | — |

TABLE 2-continued

DSC glass transition temperatures at different curing temperatures
Glass transition temperature after curing for 2 hours at different curing temperatures,
Tg(° C.)[b]

| Sample | 120° C. | 140° C. | 160° C. | 180° C. | 200° C. | 220° C. | 240° C. |
|---|---|---|---|---|---|---|---|
| D-DGEBA | — | — | — | 178 | 175 | 168 | 144 |
| D-DGEBA(I)[a] | 156 | 171 | 161 | 157 | 158 | 156 | 149 |
| J-DGEBA | — | — | — | 160 | 161 | 174 | 147 |
| J-DGEBA[d] | — | — | — | — | — | 171 | — |
| J-DGEBA(I)[a] | — | — | — | 161 | 162 | 169 | 149 |

[a]0.2 wt % (based on the epoxy resin) of the curing-promoting agent (imidazole) was added
[b]DSC measurements under nitrogen
[c]Data from reference[1]
[d]Data from reference[2]

TABLE 3

DSC glass transition temperatures at different curing temperatures
Glass transition temperature after curing for 2 hours at different
curing temperatures, Tg (° C.)[b]

| Sample | 180° C. | 200° C. | 220° C. | 240° C. |
|---|---|---|---|---|
| D-CNE | 182 | 191 | 203 | 212 |
| D-CNE(I)[a] | 200 | 203 | 210 | 192 |
| J-CNE | 137 | 139 | 160 | 199 |
| J-CNE(I)[a] | 136 | 155 | 158 | 196 |

Figure 7:
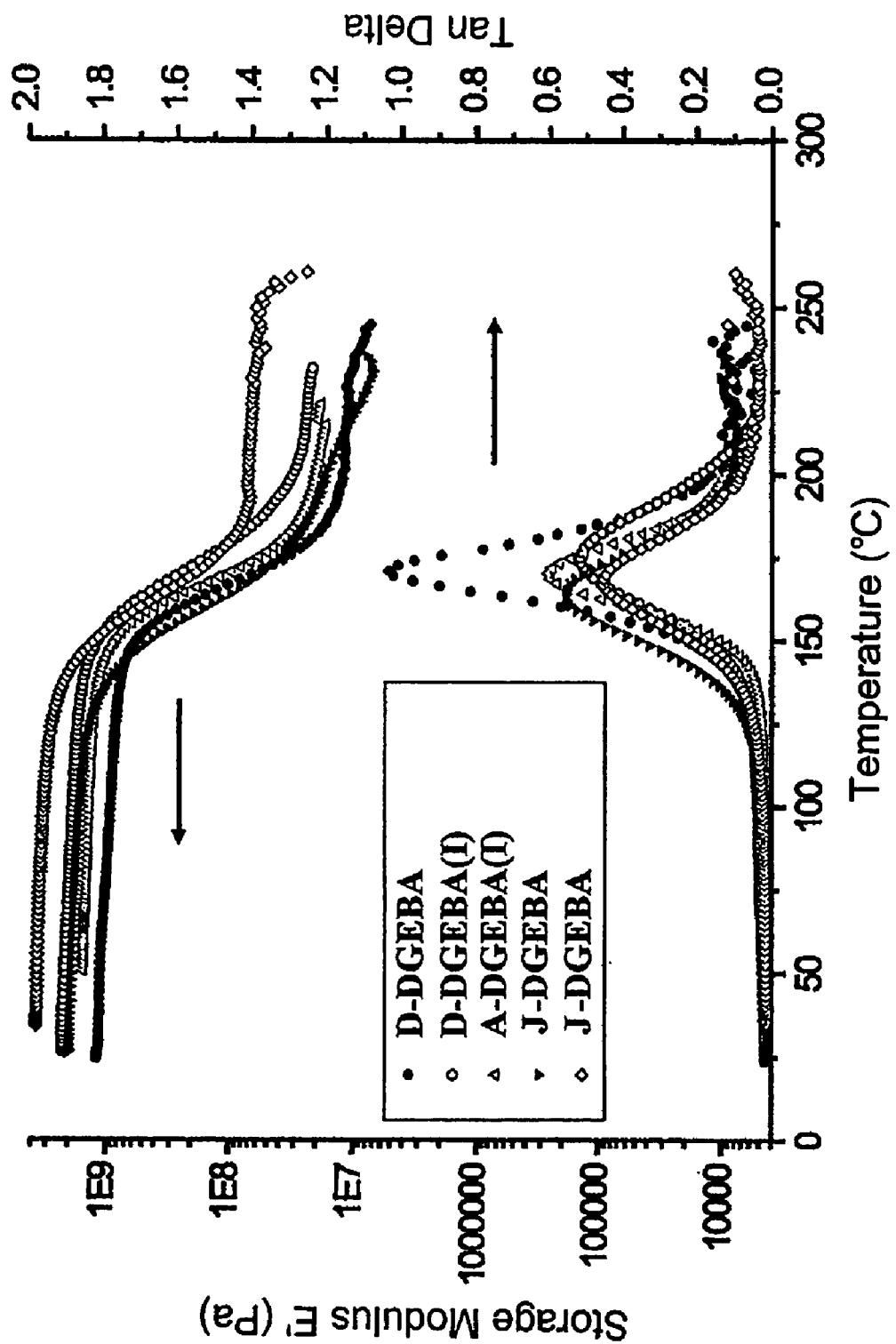
FIG. 7 shows DMA curves of DGEBA-series cured products.
Figure 8:
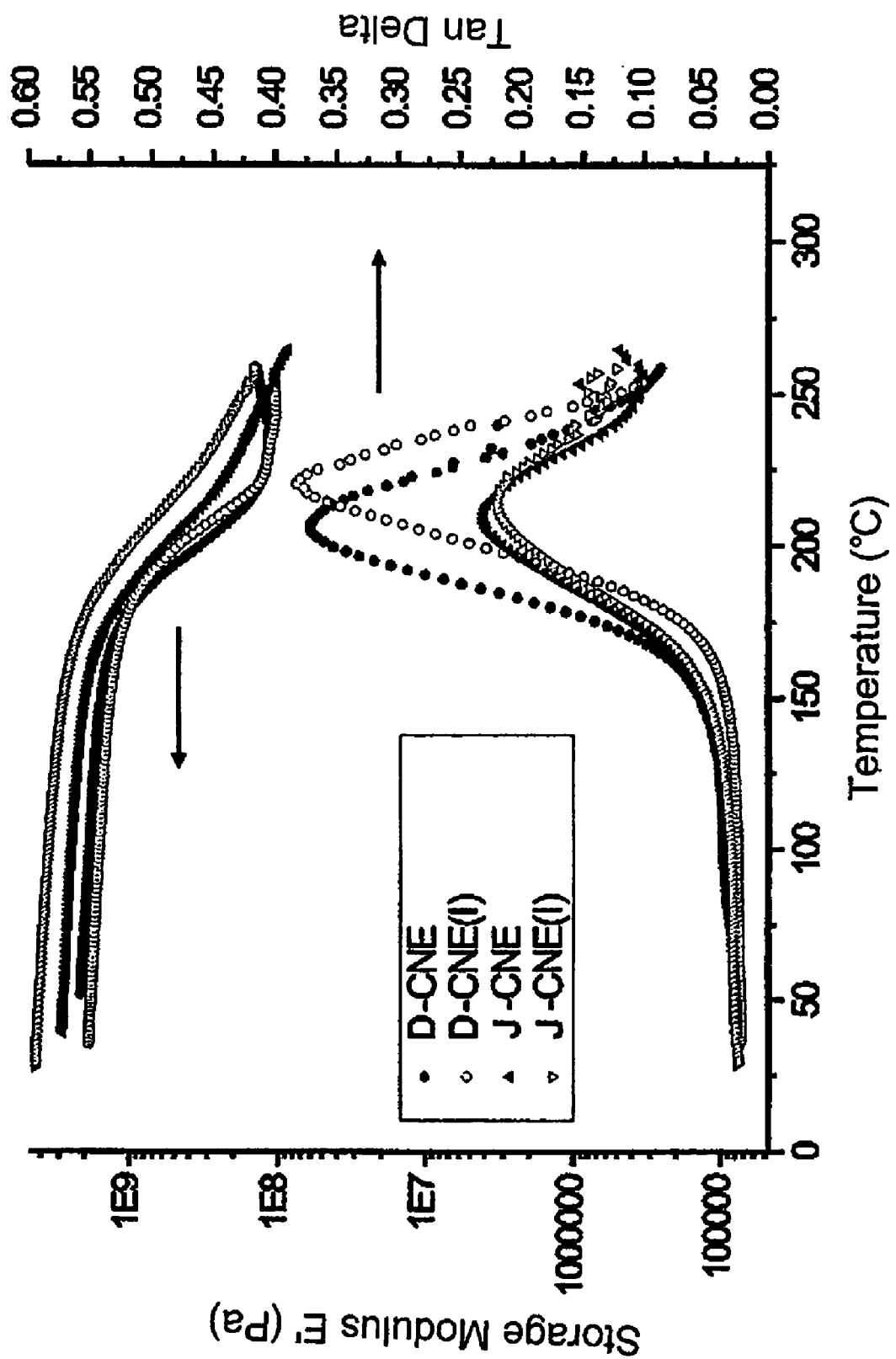
FIG. 8 shows DMA curves of CNE-series cured products.

[a]0.2 wt % (based on the epoxy resin) of the curing-promoting agent (imidazole) was added
[b]DSC measurements under nitrogen Dynamic Mechanical Analysis FIG. 7 and FIG. 8 show DMA analysis results of the DGEBA-series and CNE-series, respectively. The DMA data were summarized in Table 4 and Table 5. The analysis results show that the storage modulus of the DGEBA-series cured epoxy resins is in the following order: J-DGEBA(I)>D-DGEBA(I)>J-DGEBA>D-DGEBA>A-DGEBA(I); the storage modulus of the CNE-series cured epoxy resins is in the following order: J-CNE(I)>J-CNE>D-CNE>D-CNE(I). Although there was little difference between the storage modulus of the D-CNE and D-CNE(I), the other cured epoxy resins to which the curing-promoting agent was added have higher storage modulus. Furthermore, the cured epoxy resins to which compound J was added have the largest storage modulus, the cured epoxy resins to which the compound D was added have the second largest storage modulus, and the cured epoxy resins to which compound A was added to have the least storage modulus. It is deduced that compound A and compound D have OH groups and the OH groups become softer ethers after the compounds cross-link the epoxy resins and cure. Therefore, the storage modulus of the cured epoxy resins decreases. The same results can be obtained by an analysis of tan δ value. Because the soft cross-linked structure easily moves relative to the molecules, the tan δ height is larger. There is little difference between the glass transition temperature measured by tan δ and the glass transition temperature measured by DSC.

TABLE 4

Dynamic mechanical analysis results of DGEBA series

| Sample | Glass transition temperature Tg (° C.)[a] | tanδ[b] height | Storage modulus (GPa) |
|---|---|---|---|
| A-DGEBA(I) | 171 | 0.604 | 1.49 |
| D-DGEBA | 171 | 1.036 | 1.18 |
| D-DGEBA(I) | 175 | 0.516 | 2.21 |
| J-DGEBA | 164 | 0.557 | 1.99 |
| J-DGEBA(I) | 168 | 0.454 | 3.57 |

[a]peak height of tanδ curve
[b]tanδ value upon achieving the glass transition temperature

TABLE 5

Dynamic mechanical analysis results of the CNE series

| Sample | Glass transition temperature Tg (° C.)[a] | Tanδ[b] height | Storage modulus (GPa) |
|---|---|---|---|
| D-CNE | 205 | 0.373 | 2.13 |
| D-CNE(I) | 220 | 0.383 | 1.87 |
| J-CNE | 209 | 0.232 | 2.82 |
| J-CNE(I) | 215 | 0.222 | 4.38 |

[a]peak height of tanδ curve
[b]tanδ value upon achieving the glass transition temperature UL-94 Test UL-94 is a method for testing flame retardancy, in which a polymer sample must be subjected to two combustion processes for 10 seconds each. After the first combustion, the flame is removed and the time ($t_1$) required for self-extinguishing of the polymer is recorded. If dripping of the polymer occurs during testing, the second combustion will be carried out after cooling of the sample, and the time ($t_2$) required for self-extinguishing of the polymer and the dripping are recorded. If the sum of $t_1$ and $t_2$ is less than 10 seconds and there is no dripping, it is classified as V0 grade according to the industrial standard for flame retardancy. If the sum of $t_1$ and $t_2$ is 10-30 seconds, it is classified as V1 grade.

Two curing agents, compound D and DDS (4,4'-diaminodiphenylsulfone), were used to prepare phosphorus contents of 1%, 1.5%, and 1.8% with DGEBA and CNE, respectively. After melting at 150° C. and uniform stirring, the mixture was poured into an aluminium mold which was placed in a circulation oven where the temperature was raised stepwise up to 220° C. for curing. The cured specimens were subjected to the UL-94 flame retardancy test. Table 6 shows the results of the UL-94 test. It can be seen from table 6 that the flame retardancy of the cured epoxy resins increases with the increase of phosphorus content and V0 grade can be achieved when the phosphorus content is 1.5%.

TABLE 6

Results of UL-94 test

| Curing system | Phosphorus content (%) | Time of the first combustion (s)[a] | Time of the second combustion (s)[a] | Dripping | UL-94 grade |
|---|---|---|---|---|---|
| DGEBA/D/DDS | 1.00 | 2.44 | 18.26 | no | V1 |
| DGEBA/D/DDS | 1.50 | 3.58 | 5.28 | no | V0 |
| DGEBA/D/DDS | 1.80 | 2.56 | 4.71 | no | V0 |
| CNE/D/DDS | 1.00 | 2.13 | 12.38 | no | V1 |
| CNE/D/DDS | 1.50 | 6.47 | 3.52 | no | V0 |
| CNE/D/DDS | 1.80 | 5.50 | 0.67 | no | V0 |

[a]Average of the results of UL-94 test

The following claims are used to define the reasonable scope of the present invention. It should be appreciated that any obvious modifications achieved by those skilled in the art on the basis of the disclosure of the present invention should also fall within the reasonable scope of the present invention.

We claim:

1. A phosphorus-containing compound of general formula (I)

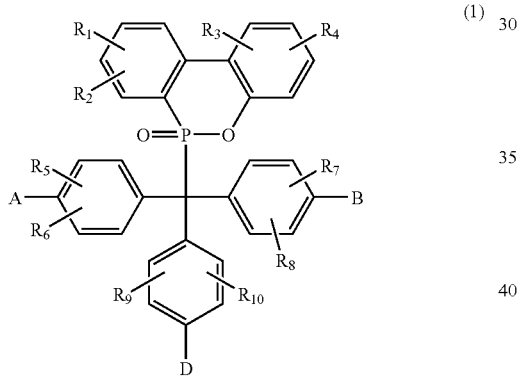

wherein $R_1$-$R_{10}$ are independently selected from the group consisting of H, $C_1$-$C_6$ alkyl, $C_1$-$C_6$ alkoxy, phenyl, nitro, phenoxy, $C_1$-$C_{10}$ halo-alkyl, $C_3$-$C_7$ cyclic alkyl, —$CF_3$, —$OCF_3$ and halogen;

A is —OH or —$NH_2$;

B is —OH or —$NH_2$;

D is selected from the group consisting of —OH, —$NH_2$, $C_1$-$C_6$ alkyl, $C_1$-$C_6$ alkoxy, $C_1$-$C_{10}$ halo-alkyl, $C_3$-$C_7$ cyclic alkyl, —$CF_3$, —$OCF_3$, halogen, —$NHR_1$, —NH(C═O)—$R_1$, —NH(O═C—O)—$R_1$, —NH(O═C—NH)—$R_1$,

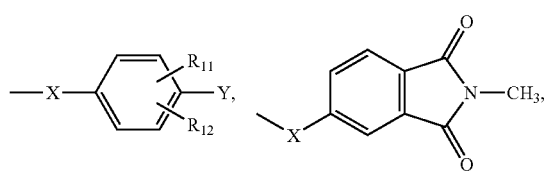

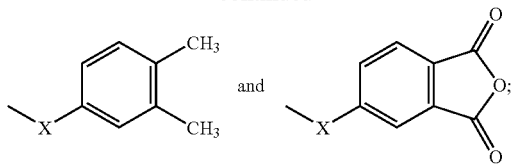

X is oxygen atom or —NH;

Y is selected from the group consisting of hydrogen, —$NO_2$, —OH, —$NH_2$, —COOH, $C_1$-$C_6$ alkyl, $C_1$-$C_6$ alkoxy, $C_3$-$C_7$ cyclic alkyl, —$CF_3$, —$OCF_3$ and halogen;

$R_{11}$-$R_{12}$ are independently selected from the group consisting of H, $C_1$-$C_6$ alkyl, $C_1$-$C_6$ alkoxy, phenyl, nitro, phenoxy, $C_1$-$C_{10}$ halo-alkyl, $C_3$-$C_7$ cyclic alkyl, —$CF_3$, —$OCF_3$ and halogen;

with the proviso that (1) when D is —OH and A and B are —$NH_2$, at least one of $R_1$-$R_{10}$ is phenyl, nitro or phenoxy; or (2) when A, B and D are —OH, (i) at least one of $R_1$-$R_{10}$ is $C_1$-$C_{10}$ halo-alkyl, —$CF_3$ or —$OCF_3$; or (ii) at least one of the combinations, ($R_1$, $R_2$), ($R_3$, $R_4$), ($R_5$, $R_6$), ($R_7$, $R_8$) and ($R_9$, $R_{10}$), is different from the other combinations; or (3) when D is selected from the group consisting of $C_1$-$C_6$ alkyl, $C_1$-$C_6$ alkoxy, $C_1$-$C_{10}$ halo-alkyl, $C_3$-$C_7$ cyclic alkyl, —$CF_3$, —$OCF_3$ and halogen, and A and B are —$NH_2$, at least one of $R_1$-$R_{10}$ is phenyl, nitro or phenoxy; or (4) when A, B and D are —$NH_2$, (i) at least one of $R_1$-$R_{10}$ is phenyl, nitro or phenoxy and at least one of the combinations, ($R_1$, $R_2$), ($R_3$, $R_4$), ($R_5$, $R_6$), ($R_7$, $R_8$) and ($R_9$, $R_{10}$), is different from the other combinations; or (ii) at least one of $R_1$-$R_{10}$ is phenyl, nitro or phenoxy and at least one of $R_1$-$R_{10}$ is $C_1$-$C_{10}$ halo-alkyl, —$CF_3$ or —$OCF_3$.

2. The compound of formula (I) according to claim 1, wherein (a) when A, B and D are —OH, $R_1$-$R_9$ are independently hydrogen, and $R_{10}$ is —$CH_3$, the compound of formula (1) is of formula (B); or

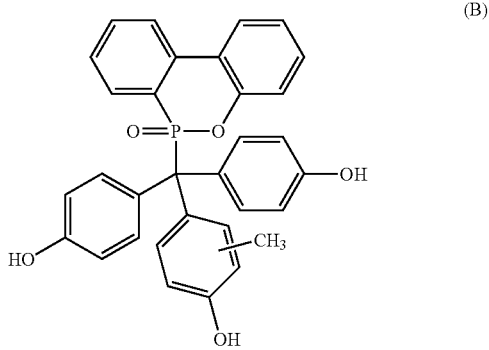

(b) when A, B and D are —OH, $R_1$-$R_8$ are independently hydrogen, and $R_9$ and $R_{10}$ are —$CH_3$, the compound of formula (1) is of formula (C); or

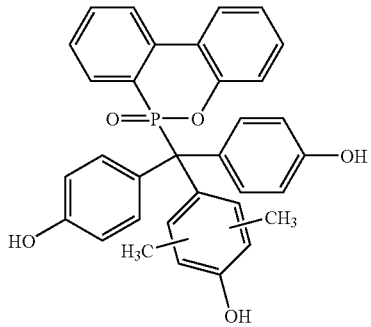

(C)

(c) when A and B are —OH, D is —$NH_2$, and $R_1$-$R_{10}$ are independently hydrogen, the compound of formula (1) is of formula (D); or

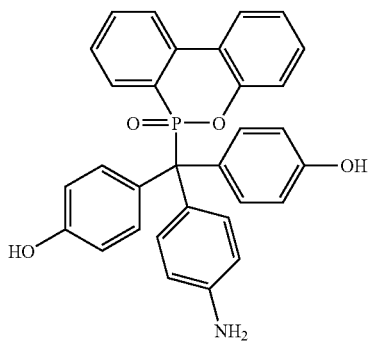

(D)

(d) when A and B are —OH, D is —$NH_2$, $R_1$-$R_9$ are independently hydrogen, and $R_{10}$ is —$CH_3$, the compound of formula (1) is of formula (E); or

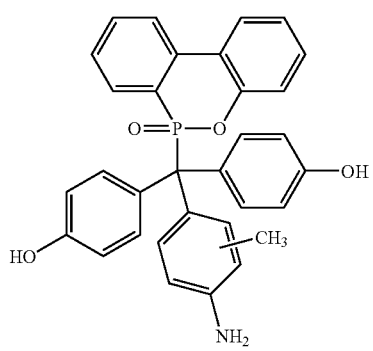

(E)

(e) when A and B are —OH, D is —$NH_2$, $R_1$-$R_8$ are independently hydrogen, and $R_9$ and $R_{10}$ are —$CH_3$, the compound of formula (1) is of formula (F)

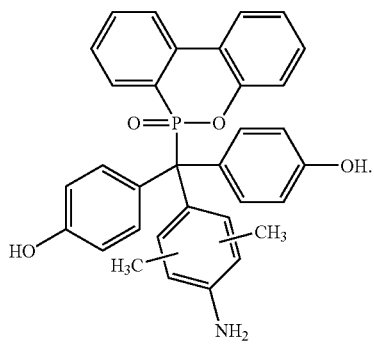

(F)

3. A process of preparing the compound of formula (1) according to claim 1, comprising reacting an organophosphorous compound of formula (2) and a compound of formula (3) with a compound of formula (4) in the presence of an acid catalyst to form the compound of formula (1);

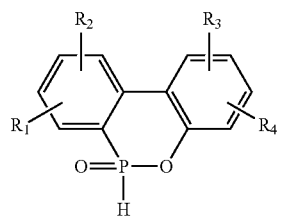

(2)

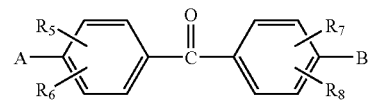

(3)

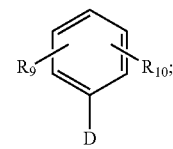

(4)

wherein $R_1$-$R_{10}$, A, B and D are as defined in claim 1.

4. The process according to claim 3, comprising
(a) when A, B and D are —OH, and $R_1$-$R_{10}$ are hydrogen, reacting 9,10-dihydro-9-oxa-10-phosphaphenanthrene-10-oxide (DOPO) of formula (2) and 4,4'-dihydroxy benzophenone (DHBP) of formula (3) with phenol of formula (4) in the presence of an acid catalyst to form the compound of formula (A);

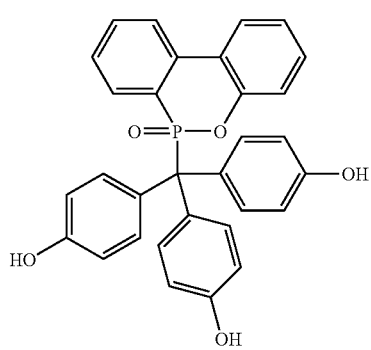

(A)

(b) when A, B and D are —OH, $R_1$-$R_9$ are hydrogen, and $R_{10}$ is —CH$_3$, reacting 9,10-dihydro-9-oxa-10-phosphaphenanthrene-10-oxide (DOPO) of formula (2) and 4,4'-dihydroxy benzophenone (DHBP) of formula (3) with 2-cresol of formula (4) in the presence of an acid catalyst to form the compound of formula (B);

(c) when A, B and D are —OH, $R_1$-$R_8$ are hydrogen, and $R_9$ and $R_{10}$ are —CH$_3$, reacting 9,10-dihydro-9-oxa-10-phosphaphenanthrene-10-oxide (DOPO) of formula (2) and 4,4'-dihydroxy benzophenone (DHBP) of formula (3) with 2,6-dimethylphenol of formula (4) in the presence of an acid catalyst to form the compound of formula (C);

(d) when A and B are —OH, D is —NH$_2$, and $R_1$-$R_{10}$ are hydrogen, reacting 9,10-dihydro-9-oxa-10-phosphaphenanthrene-10-oxide (DOPO) of formula (2) and 4,4'-dihydroxy benzophenone (DHBP) of formula (3) with aniline of formula (4) in the presence of an acid catalyst to form the compound of formula (D);

(e) when A and B are —OH, D is —NH$_2$, $R_1$-$R_9$ are hydrogen, and $R_{10}$ is —CH$_3$, reacting 9,10-dihydro-9-oxa-10-phosphaphenanthrene-10-oxide (DOPO) of formula (2) and 4,4'-dihydroxy benzophenone (DHBP) of formula (3) with o-toluidine of formula (4) in the presence of an acid catalyst to form the compound of formula (E);

(f) when A and B are —OH, D is —NH$_2$, $R_1$-$R_8$ are hydrogen, and $R_9$ and $R_{10}$ are —CH$_3$, reacting 9,10-dihydro-9-oxa-10-phosphaphenanthrene-10-oxide (DOPO) of formula (2) and 4,4'-dihydroxy benzophenone (DHBP) of formula (3) with 2,6-dimethylaniline of formula (4) in the presence of an acid catalyst to form the compound of formula (F);

(g) when A and B are —NH$_2$, D is —OH, and $R_1$-$R_{10}$ are hydrogen, reacting 9,10-dihydro-9-oxa-10-phosphaphenanthrene-10-oxide (DOPO) of formula (2) and 4,4'-diamino benzophenone (DABP) of formula (3) with phenol of formula (4) in the presence of an acid catalyst to form the compound of formula (G);

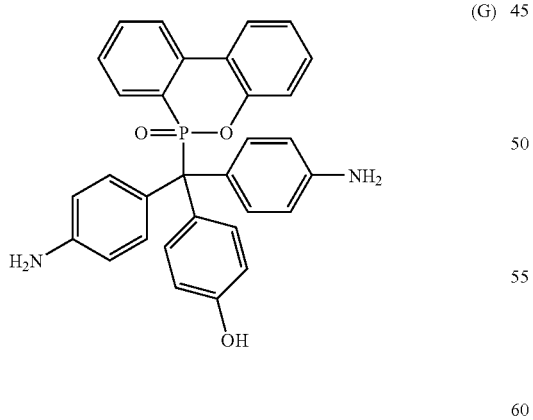

(h) when A and B are —NH$_2$, D is —OH, $R_1$-$R_9$ are hydrogen, and $R_{10}$ is —CH$_3$, reacting 9,10-dihydro-9-oxa-10-phosphaphenanthrene-10-oxide (DOPO) of formula (2) and 4,4'-diamino benzophenone (DABP) of formula (3) with 2-cresol of formula (4) in the presence of an acid catalyst to form the compound of formula (H);

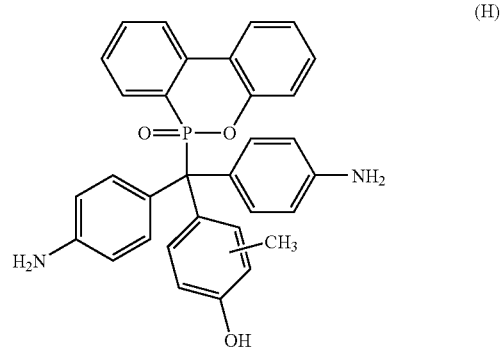

(i) when A and B are —NH$_2$, D is —OH, $R_1$-$R_8$ are hydrogen, and $R_9$ and $R_{10}$ are —CH$_3$, reacting 9,10-dihydro-9-oxa-10-phosphaphenanthrene-10-oxide (DOPO) of formula (2) and 4,4'-diamino benzophenone (DABP) of formula (3) with 2,6-dimethylphenol of formula (4) in the presence of an acid catalyst to form the compound of formula (I);

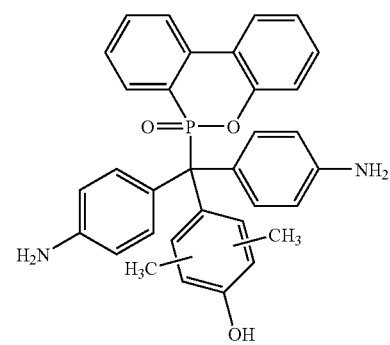

(j) when A, B and D are —NH$_2$, and $R_1$-$R_{10}$ are hydrogen, reacting 9,10-dihydro-9-oxa-10-phosphaphenanthrene-10-oxide (DOPO) of formula (2) and 4,4'-diamino benzophenone (DABP) of formula (3) with aniline of formula (4) in the presence of an acid catalyst to form the compound of formula (J);

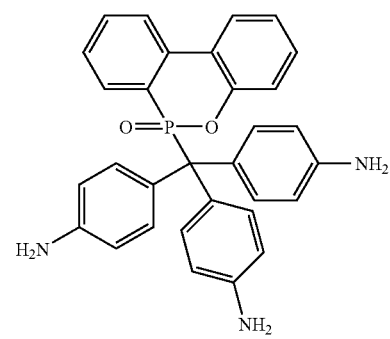

(k) when A, B and D are —NH$_2$, $R_1$-$R_9$ are hydrogen, and $R_{10}$ is —CH$_3$, reacting 9,10-dihydro-9-oxa-10-phosphaphenanthrene-10-oxide (DOPO) of formula (2) and 4,4'-diamino benzophenone (DABP) of formula (3) with o-toluidine of formula (4) in the presence of an acid catalyst to form the compound of formula (K);

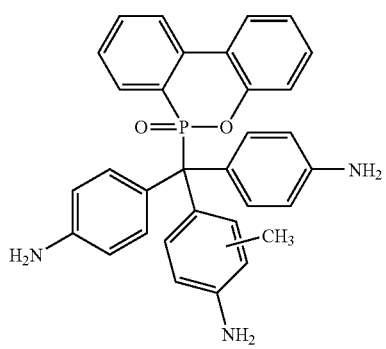

(K)

(l) when A, B and D are —NH$_2$, R$_1$-R$_8$ are hydrogen, and R$_9$ and R$_{10}$ are —CH$_3$, reacting 9,10-dihydro-9-oxa-10-phosphaphenanthrene-10-oxide (DOPO) of formula (2) and 4,4'-diamino benzophenone (DABP) of formula (3) with 2,6-dimethylaniline of formula (4) in the presence of an acid catalyst to form the compound of formula (L)

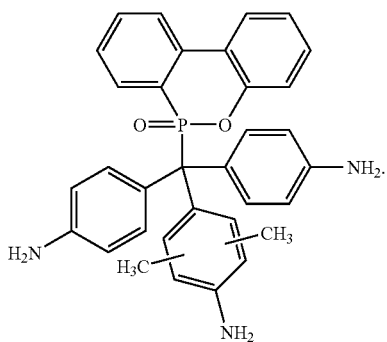

(L)

5. The process according to claim 3, wherein R$_1$-R$_{10}$ are hydrogen, comprising
 (a) when A is —NH$_2$ and B and D are —OH, reacting 9,10-dihydro-9-oxa-10-phosphaphenanthrene-10-oxide (DOPO) of formula (2) and 4-amino-4'-hydroxy benzophenone (AHBP) of formula (3) with phenol of formula (4) in the presence of an acid catalyst to form the compound of formula (D);
 (b) when A and D are —NH$_2$ and B is —OH, reacting 9,10-dihydro-9-oxa-10-phosphaphenanthrene-10-oxide (DOPO) of formula (2) and 4-amino-4'-hydroxy benzophenone (AHBP) of formula (3) with aniline of formula (4) in the presence of an acid catalyst to form the compound of formula (G).

6. The process according to claim 3, wherein the acid catalyst is selected from the group consisting of protic acids and Lewis acids.

7. The process according to claim 4, wherein the acid catalyst is selected from the group consisting of protic acids and Lewis acids.

8. The process according to claim 5, wherein the acid catalyst is selected from the group consisting of protic acids and Lewis acids.

9. The process according to claim 3, wherein the acid catalyst is selected from the group consisting of acetic acid, p-toluenesulfonic acid (PTSA), methanesulfonic acid, calmagite, sulfuric acid, orthanilic acid, 3-pyridinesulfonic acid, sulfanilic acid, hydrogen chloride (HCl), hydrogen bromide (HBr), hydrogen iodide (HI), hydrogen fluoride (HF), trifluoroacetic acid (CF$_3$COOH), nitric acid (HNO$_3$), phosphoric acid (H$_3$PO$_4$), aluminum chloride (AlCl$_3$), boron fluoride (BF$_3$), ferric bromide (FeBr$_3$), ferric chloride (FeCl$_3$), boron chloride (BCl$_3$), and titanium chloride (TiCl$_4$).

10. The process according to claim 4, wherein the acid catalyst is selected from the group consisting of acetic acid, p-toluenesulfonic acid (PTSA), methanesulfonic acid, calmagite, sulfuric acid, orthanilic acid, 3-pyridinesulfonic acid, sulfanilic acid, hydrogen chloride (HCl), hydrogen bromide (HBr), hydrogen iodide (HI), hydrogen fluoride (HF), trifluoroacetic acid (CF$_3$COOH), nitric acid (HNO$_3$), phosphoric acid (H$_3$PO$_4$), aluminum chloride (AlCl$_3$), boron fluoride (BF$_3$), ferric bromide (FeBr$_3$), ferric chloride (FeCl$_3$), boron chloride (BCl$_3$), and titanium chloride (TiCl$_4$).

11. The process according to claim 5, wherein the acid catalyst is selected from the group consisting of acetic acid, p-toluenesulfonic acid (PTSA), methanesulfonic acid, calmagite, sulfuric acid, orthanilic acid, 3-pyridinesulfonic acid, sulfanilic acid, hydrogen chloride (HCl), hydrogen bromide (HBr), hydrogen iodide (HI), hydrogen fluoride (HF), trifluoroacetic acid (CF$_3$COOH), nitric acid (HNO$_3$), phosphoric acid (H$_3$PO$_4$), aluminum chloride (AlCl$_3$), boron fluoride (BF$_3$), ferric bromide (FeBr$_3$), ferric chloride (FeCl$_3$), boron chloride (BCl$_3$), and titanium chloride (TiCl$_4$).

12. The process according to claim 3, wherein the amount of the acid catalyst used is 0.1 wt %-30 wt % of the amount of the organophosphorous compound.

13. The process according to claim 4, wherein the amount of the acid catalyst used is 0.1 wt %-30 wt % of the amount of the organophosphorous compound.

14. The process according to claim 5, wherein the amount of the acid catalyst used is 0.1 wt %-30 wt % of the amount of the organophosphorous compound.

15. A curing agent comprising the compound according to claim 1 or a mixture thereof.

16. A flame resistant epoxy resin comprising an epoxy resin and the curing agent according to claim 15.

17. The flame resistant epoxy resin according to claim 16, wherein the epoxy resin is diglycidyl ether of bisphenol A (DGEBA) or o-cresol formaldehyde novolac epoxy resin (CNE).

18. A process of preparing the flame resistant epoxy resin comprising an epoxy resin and the curing agent according to claim 15, comprising uniformly mixing an epoxy resin and the curing agent according to claim 15 in an equivalent proportion of 1:0.1 to 1:1 and curing to obtain the cured and flame resistant epoxy resin.

19. The process according to claim 18, wherein the epoxy resin is diglycidyl ether of bisphenol A (DGEBA) or o-cresol formaldehyde novolac epoxy resin (CNE).

* * * * *